United States Patent
Harley et al.

(10) Patent No.: US 6,232,522 B1
(45) Date of Patent: *May 15, 2001

(54) NON-HUMAN ANIMAL MODEL FOR SYSTEMIC LUPUS ERYTHEMATOSIS

(75) Inventors: John B. Harley; Judith A. James; R. Hal Scofield, all of Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/160,604

(22) Filed: Nov. 30, 1993

Related U.S. Application Data

(63) Continuation-in-part of application No. 07/867,819, filed on Apr. 13, 1992, now abandoned, which is a continuation-in-part of application No. 07/648,205, filed on Jan. 31, 1991, now abandoned, which is a continuation-in-part of application No. 07/472,947, filed on Jan. 31, 1990, now abandoned.

(51) Int. Cl.[7] ............................. C07K 5/00; A61K 38/00; C12N 15/85

(52) U.S. Cl. ................................ 800/9; 514/2; 530/387.1; 530/403; 530/387.2; 435/325; 435/335; 435/375; 435/352; 435/7.2; 435/555; 800/11

(58) Field of Search ................................... 435/172, 375, 435/7.2, 325, 335, 352, 355; 424/185.1, 9; 530/328, 330, 387.9, 387.1, 403, 387.2; 800/9, 11

(56) References Cited

U.S. PATENT DOCUMENTS

| | | | |
|---|---|---|---|
| 4,554,101 | 11/1985 | Hopp | 514/17 |
| 4,784,942 | 11/1988 | Harley | 424/85.8 |
| 4,865,970 | 9/1989 | Brot et al. | 435/7 |
| 5,312,752 | 5/1994 | Wotiz et al. | 435/240.27 |
| 5,354,691 | 10/1994 | Van Eden et al. | 436/506 |

FOREIGN PATENT DOCUMENTS

| | | | |
|---|---|---|---|
| 0313156 | 4/1989 | (EP) | |
| WOA88/09932 | 6/1988 | (WO) | |
| WOA91/11718 | 8/1991 | (WO) | |
| WO91/17171 | 11/1991 | (WO) | C07H/15/12 |
| WO 94/02445 | 2/1994 | (WO) | C07C/237/06 |
| WO 94/02509 | 2/1994 | (WO) | C07K/7/06 |

OTHER PUBLICATIONS

Alexander, et al., "Anti–Ro/SS–A Antibodies in the Pathophysiology of Congenital Heart Block in Neonatal Lupus Syndrome, an Experimental Model," Arth. and Rheum. 35:176–189 (1992).

Baraket, et al., "Recognition of synthetic peptides of Sm–D autoantigen bu lupus sera," Clin. Exp. Immunol. 81:256–262 (1990).

Blank, M., et al., "The effect of the immunomodulator agent AS101 on interleukin–2 production in systemic lupus erythematosus (SLE) induced in mice by a pathogenic anti–DNA antibody," Clin. Exp. Immunol. 79:443–447 (1990).

Blank, M., et al., "Induction of SLE–like disease in naive mice with a monoclonal anti–DNA antibody derived from a patient with polymyositis carrying the 16/6 ld," J. Autoimmunity 1:683–691 (1988).

Blank, M., et al., "Sex hormone involvement in the induction of experimental systemic lupus erythematosus by a pathogenic anti–DNA idiotype in naive mice," J. Rheumatol. 17:311–317 (1990).

Blank, M., et al., "Induction of systemic lupus erythematosus in naive mice with T–cell lines specific for human anti–DNA antibody SA–1 (16/6 ld+) and for mouse tuberculosis antibody TB/68 (16/6 ld+)," Clin. Immunol. Immunopathol. 60:471–483 (1991).

Blank, M., et al., "Induction of experimental anti–phospholipid syndrome associated with SLE following immunization with human monoclonal pathogenic anti–DNA idiotype," J. Autoimmunity 5:495–509 (1992).

Buyon, "Neonatal lupus syndromes," Curr. Opin. in Rheum. 6:523–529 (1994).

Craft, et al., "Murine and Drosophila B Proteins of SM snRNPS," Mol. Biol. Rep. 15:159 (1991).

Deutscher, et al., "Molecular analysis of the 60–kDa human Ro ribonucleoprotein," Proc. Natl. Acad. Sci. USA 85:9479–83 (1988).

Esquivel, et al., "Induction of Autoimmunity in Good and Poor Responder Mice with Mouse Thyrobglobulin and Lipopolysaccharide," J. Exp. Med. 145:1250–1263 (1977).

Fricke, H., et al., "Induction of experimental systemic erythematosus in mice by immunization with a monoclonal anti–La autoantibody," Intern. Immunol. 2:225–230 (1990).

(List continued on next page.)

Primary Examiner—Karen M. Hauda
Assistant Examiner—Anne Marie S. Beckerleg
(74) Attorney, Agent, or Firm—Arnall Golden & Gregory, LLP

(57) ABSTRACT

A specific method has been developed to produce an autoimmune response and resulting clinical symptoms for a particular disease process. Peptides or other structures derived from an autoantigen and which are bound by auto antibody or T cell receptors are identified and used to induce an immune response. This immune response evolves into an autoimmune response directed against the other portions of the protein from which the peptide was derived. Subsequently, clinical manifestations may appear that are also found in the clinical illness. selected from the group including viruses, bacteria, fungi, parasites, rickettsia, plasmids, and insects which contains a structure or a peptide sequence that is similar to a structure or peptide sequence that has been identified by the method of claim 1 to the extent that it is bound by one of the group selected from antigen specific B cell surface receptors, and antigen specific T cell receptors.

13 Claims, 9 Drawing Sheets

OTHER PUBLICATIONS

Fritz, et al., "Small Nuclear U–Ribonucleoproteins in *Xenopus laevis* Development," *J. Mol. Biol.* 178:273–285 (1984).

Gaither, et al., "Affinity Purification and Immunoassay of Anti–Ro/SSA," *Protides Biol. Fluids* 33:413–416 (1985).

Geysen, et al., "Use of peptide synthesis to probe viral antigens for epitopes to a resolution of a single amino acid," *Proc. Natl. Acad. Sci. USA* 81:3998–4002 (1984).

Harley, et al., "Anti–Ro (SS–A) and Anti–La (SS–B) in Patients with Sjogren's Syndrome," *Arthritis Rheum.* 29:196–206 (1986).

Harley, et al., "Autoantibodies," *Rheum. Dis. Clin. North Amer.* 14:43–56 (1988).

Hinterberger, et al., "Isolation of Small Nuclear Ribonucleoproteins Containing U1, U2, U4, U5, and U6 RNAs," *J. Biol. Chem.* 258:2604–2613 (1983).

Horsfall, et al., "Ro and La Antigens and Maternal Anti–La Idiotype on the Surface of Myocardial Fibres in Congenital Heart Block," *J. of Autoimmun.* 4:165–176 (1991).

Huang, et al., "Human Anti–Ro Autoantibodies Bind Peptides Accessible to the Surface of the Native Ro Autoantigen," *Scand. J. Immunol.* 41:220–228 (1995).

Huang, et al., "Immunization with Vesicular Stomatitis Virus Nucleocapsid Protein Induces Autoantibodies to the 60 kD Ro Ribonucleoprotein Particle," *J. Investig. Med.* 43:151–158 (1995).

James, et al., "Immunoglobulin Epitope Spreading and Autoimmune Disease After Peptide Immunization: Sm B/B'–derived PPPGMRPP and PPPGIRGP Induce Spliceosome Autoimmunity," *J. of Exp. Med.* 181:453–461 (1995).

James, et al., "Sequential autoantigenic determinants of the small nuclear ribonucleoprotein Sm D shared by human lupus autoantibodies and MRL lpr/lpr antibodies," *Clin. Exp. Immunol.* 98:419–426 (1994).

James and Harley, "Peptide autoantigenicty of the small nuclear ribonucleoprotein C," *Clin. and Exp. Rheum.* 13:299–305 (1995).

James and Harley, "Sequential Fine Specificity of the Small Nuclear Ribonuclear Protein C," *Clinical Res.* 41(2):PA393 (1993).

James, et al., "Basic Amino Acids Predominate in the Sequential Autoantigenic Determinants of the Small Nuclear 70K Ribonucleoprotein," *Scand. J. Immunol.* 39:557–566 (1994).

James and Harley, "Human Lupus Anti–Spliceosome A Autoantibodies Bind Contiguous Surface Structures and Segregate into Two Sequential Epitope Binding Patterns," (Submitted to *J. Immunol.* Oct. 23, 1995).

Kalush, et al., "Neonatal Lupus Erythematosus with Cardiac Involvement in Offspring of Mothers with Experimental Systemic Lupus Erythematosus," *J. of Clin. Immunol.* 14:314–321 (1994).

Lee, et al., "Cardiac Immunoglobulin Deposition in Congenital Heart Block Associated with Maternal Anti–Ro Autoantibodies," *Am. J. of Med.* 83:793–796 (1987).

Lehmann, et al., "Spreading of T–cell autoimmunity to cryptic determinants of an autoantigen," *Nature* 356:155–157 (1992).

Lerner, et al., "Are snRNPs involved in splicing?" *Nature* 283:220–224 (1980).

Maddison, et al., "Quantitation of Precipitating Antibodies to Certain Soluble Nuclear Antigens in SLE," *Arthritis Rheum.* 20:819–824 (1977).

Manfredi, et al., "Molecular anatomy of an autoantigen: T and B epitopes on the nicotinic acetylcholine receptor in myasthenia gravis," *J. Lab. Clin. Med.* 120:13–21 (1992).

Matter, et al., "Molecular Characterization of Ribonucleoprotein Antigens Bound by Antinuclear Antibodies," *Arthritis Rheum.* 25:1278–1283 (1982).

Mattioli, et al., "Physical Association of Two Nuclear Antigens and Mutual Occurrence of Their Antibodies: The Relationship of the SM and RNAProtein (MO) Systems in SLE Sera," *J. Immunol.* 110:1318–1324 (1973).

Mendlovic, S., et al., "The genetic regulation of the induction of experimental SLE," *Immunology* 69:228–236 (1990).

Mendlovic, S., et al., "The role of anti–idiotypic antibodies in the induction of experimental systemic lupus erythematosus in mice," *Eur. J. Immunol.* 19:729–732 (1989).

Mendlovic, S., et al., "Induction of an SLE–like disease in mice by a common anti–DNA idiotype," *Proc. Natl. Acad. Sci. USA* 85:2260–2264 (1988).

Miller, et al., "The role of an autoantigen, histidyl–tRNA synthetase, in the induction and maintenance of autoimmunity," *Proc. Natl. Acad. Sci. USA* 87:9933–9937 (1990).

Munves, et al., "Antibodies to Sm and RNP," *Arthritis Rheum.* 26:848–853 (1983).

Ohosone, et al., "Molecular cloning of cDNA encoding Sm autoantigen: Derivation of a cDNA for a B polypeptide of the U series of small nuclear ribonucleoprotein particles," *Proc. Natl. Acad. Sci. USA* 86:4249–4253 (1989).

Palfi, et al., "Purification of the major UsnRNPs from broad bean nuclear extracts and characterization of their protein constituents," *Nucleic Acids Res.* 17:1445–1458 (1989).

Query, et al., "A Common RNA Recognition Motif Identified within a Defined U1 RNA Binding of the 70K U1 snRNP Protein," *Cell* 57:89–101 (1989).

Reichlin, et al., "Autoantibodies to the URNP particles: relationship to clinical diagnosis and nephritis," *Clin. Exp. Immunol.* 83–286–290 (1991).

Reichlin, et al., "Concentration of Autoantibodies to Native 60–kd Ro/SS–A and Denatured 52–kd Ro/SS–A in Eluates from the Heart of a Child Who Died with Congenital Complete Heart Block," *Arth. and Rheum.* 37:1698–1703 (1994).

Rokeach, et al., "Molecular cloning of a cDNA encoding the human Sm–D autoantigen," *Proc. Natl. Acad. Sci. USA* 85:4832–36 (1988).

Rose, et al., "T–Cell Regulation in Autoimmune Thyroiditis," *Immunol. Reviews* 55:229–314 (1981).

Rose, et al., "Genetic Regulation in Autoimmune Thyroiditis," Talal N. ed. *Autoimmunology Genetic, Immunologic Virologic, and Clinical Aspects,* New York: Academic Press, 63–87 (1977).

Rose, et al., "Studies on Experimental Thyroiditis," *Ann. NY Acad. Sci.* 124: 201–108 (1965).

Schmauss, et al., "A comparison of snRNP–associated SM–autoantigens: human N, rat N and human B/B'," *Nucleic Acids Res.* 17:1733–1743 (1989).

Scofield, R.H. and Harley, J.B., "Autoantigenicity of Ro/SSA antigen is related to a nucleocapsid protein of vesicular stomatitis virus," *Proc. Natl. Acad. Sci. USA* 88:3343–3347 (1991).

Shoenfeld, et al., "Pathogenic idiotypes of autoantibodies in autoimmunity: lessons from new experimental models of SLE," *FASEB J.* 4:2646–2651 (1990).

Shoenfeld, Y., "Modulation of experimental SLE induced in naive mice by a pathogenic anti–DNA idiotype (16/6 ld.)," *Proceedings of the Second International conference on Systemic Lupus Erythematosus* Tokyo, Japan Professional Postgraduate Services 83 (1989).

Sillekens, et al., "Human U1 snRNP–specific C protein: complete cDNA and protein sequence and identification of a multigene family in mammals," *Nucleic Acids Res.* 16:8307–21 (1988).

Spritz, et al., "The human U1–70K sn RNP protein: cDNA cloning, chromosomal localization, expression, alternative splicing and RNA–binding," *Nucleic Acid Res.* 15:10373–91 (1987).

Tan, et al., "The 1982 Revised Criteria for the Classification of Systemic Lupus Erythematosus," *Arthritis Rheum.* 25:1271–77 (1982).

Tan, et al., "Characteristics of a Soluble Nuclear Antigen Precipitating with Sera of Patients with Systemic Lupus Erythematosus," *J. Immunol.* 96:464–471 (1966).

Theissen, et al., "Cloning of the human cDNA for the U1 RNA–associated 70K protein," *EMBO J.* 5:3209–17 (1986).

Tincani, et al., "Induction of experimental SLE in naive mice by immunization with human polyclonal anti–DNA antibody carrying the 16/6 idiotypic," *Clinical and Exp. Rheum.* 11:129–134 (1993).

Tzartos, et al., *Autoimmunity* 8:259–270 (1991).

van Dam, et al., "Cloned human snRNP proteins B and B' differ only in their carboxy–terminal part," *EMBO J.* 8:3853–3860 (1989).

Waite, K., et al., "Anti–Jo–1 antibodies are directed at an evolutionarily–conserved, conformational site on human histidyl–tRNA synthetase," *Mol. Cell Biol. Autoantibodies Autoimm.* 100–101 (1989).

Waltuck and Buyon, "Autoantibody–associated Congenital Heart Block: Outcome in Motehrs and Children," *Ann. Intern. Med.* 120:544–551 (1994).

Watson et al., "Certain Properties Make Substances Antigenic," *Molecular Biology of the Gene,* Fourth Edition, p. 836, paragraph 3, (The Benjamin/Cummings Publishing Company, Menlo Park, 1987).

Williams, et al., "A Repeated Proline–rich Sequence in Sm B/B' and N is a Dominant Epitope Recognized by Human and Murine Autoantibodies," *J. Autoimmunity* 3:715–725 (1990).

Winfield, et al., "Serologic Studies in Patients with Systemic Lupus Erythematosus and Central Nervous System Dysfunction," *Arthritis Rheum.* 21:289–294 (1978).

Witebsky, et al., "Chronic Thyroiditis and Autoimmunization," *J. Am. Med. Assoc.* 164:1439–1447 (1957).

Zeller, et al., "Nucleocytoplasmic Distribution of snRNPs and Stockpiled snRNA–Binding Proteins during Oogenesis and Early Development in *Xenopus laevis,*" *Cell* 32:425–434 (1983).

*The Medical Letter on Drugs and Therapeutics* 37(951):55–57 (Jun. 23, 1995).

Barakat, et al., "IgG antibodies from patients with primary Sjogren's syndrome and systemic lupus erythematosus regcognize different epitopes in 60–kD SSA/Ro protein," *Clin. Exp. Immunol.* 89:38–45 (1992).

Dyrberg and Oldstone, "Peptides as Probes to Study Molecular Mimicry and Virus–Induced Autoimmunity," *Current Topics in Microbiology and Immunology* 130:25–37 (1986).

Geysen, et al., "Strategies for epitope analysis using peptide synthesis," *J. of Immunol. Meth.* 102:259–274 (1987).

Herbert, et al., *Dictionary of Immunology* 3rd Edition, Blackwell Scientific Publications, Oxford, UK, p. 14 (1985).

Banerjee, et al., "Complete Nucleotide Sequence of the mRNA Coding for the N Protein of Vesicular Stomatitis Virus (New Jersey Serotype)," *Virology* 137:432–438 (1984).

Cohen, "The Self, the World and Autoimmunity," *Scientific American* 258:52–60 (1988).

DePolo, et al., "continuing Coevolution of Virus and Defective Interfering Particles and of Viral Genome Sequences during Undiluted Passages: Virus Mutants Exhibiting Nearly Complete Resistance to Formerly Dominant Defective Interfering Particles," *J. of Virology* 61:454–464 (1987).

Gallione, et al., *Virology* 39:529–535 (1981).

Voller and Bidwell, "Enzyme–Linked Immunosorbent Assay," *Manual of Clinical Laboratory Immunology* (Chapter 17) (1986).

Virji and Heckels, "Location of a Blocking Epitope on Outer–membrane Protein III of *Neisseria gonorrhoeae* by Synthetic Peptide Analysis," *J. of Gen. Microbiol.* 135:1895–1899 (1989).

James, Judith A. and John B. Harley, "Linear Epitope Mapping of an Sm B/B' Polypeptide," *J. of Immun.* 148:2074–2079 (1992).

Ben–Chatrit, Eldad, et al., "Isolation and Characterization of a cDNA Encoding the 60–kD Component of the Human SS–A/Ro Ribonucleoprotein Autoantigen," *J. Clin. Inv.* 83:1284–1292.

Chambers, Jasemine C., et al., "Genomic Structure and Amino Acid Sequence Domains of the Human La Autoantigen," *J. Biol. Chem.* 263:18043–18051 (1988).

Chambers, Jasemine Choy and Jack D. Keene, "Isolation and analysis of cDNA clones expressing human lupus La antigen," *Proc. Natl. Acad. Sci. USA* 82:2115–2119 (1985).

Ferris and Donaldson, *Veterinary Microbiology* vol. 18 No. 3–4, pp. 243–258 (1988).

Mosier, et al., *Nature* vol. 335, pp. 256–259 (1988).

Dickey, W.D., *Human Autoantibody Producing Grafts in SCID Mice,* presented to the Oklahoma Lupus Association, Sep. (1989) (Abstract).

Yamamoto, K., et al., "Isolation and Characterization of a Complementary DNA Expressing Human U1 Small Nuclear Ribonucleoprotein C Polypeptide", *Journal of Immunology,* 140(1):311–317 (1988).

Tigbe, Production of human rheumatoid factors (RF) by SCID mice transplanted with synovial membrane lymphocytes, presented at the Arthritis Foundation Fellows Conference, Amelia Island, Plantation, Florida, Dec. 8–10, 1989.

Guldner, et al., *The Journal of Immunology,* vol. 141, No. 2, pp. 469–475 (Jul. 15, 1988).

Schaack, pp. 581–588, In *Annals of Internal Medicine* vol. 111, No. 7, pp. 581–591 (Oct. 1, 1989).

Chan, E.K.L., et al., "Ribonucleoprotein SS–B/La Belongs to a Protein Family with Consensus Sequence for RNA Binding",, *Nucleic Acids Research,* 17(6):2233–2244 (1989).

Crone, et al., "Viral Transcription is Necessary and Sufficient for Vesicular Stomatis Virus to Inhibit Maturation of Small Nuclear Ribonucleoproteins", *Journal of Virology,* 63(10):4172–4180 (1989).

Cunningham, et al., "Human Monoclonal Antibodies Reactive with Antigens of the Group A Streptococcus and Human Heart", *Journal of Immunology,* 141(8):2760–2766, (1988).

Elkon, K.B., et al., "Epitope Mapping of Recombinant HeLa SmB and B' Peptides Obtained by the Polymerase Chain Reaction", *Journal of Immunology,* 145(2):636–643 (1990).

Harley, et al., "Gene Interaction at HLA–DQ Enhances Autoantibody Production in Primary Sjorgren's Syndrome", *Science,* 232:1145–1147 (1986).

Kurilla, et al., "The Leader RNA of Vesicular Stomatis Virus is Bound by a Cellular Protein Reactive with Anti–La Lupus Antibodies", *Cell,* 34:837–845 (1983).

McAllister, G., et al., "cDNA Sequence for the Rat U snRNP–Associated Protein N: Description of a Potential Sm Epitope", *EMBO Journal,* 8(4):1177–1181 (1989).

Renz, M., et al., "Expression of the Major Human Ribonucleoprotein (RNP) Autoantigens of *Escherichia coli* and Their Use in an EIA for Screening Sera from Patients with Autoimmune Diseases", *Clinical Chemistry,* 35(9):1861–1863 (1989).

Rokeach, L.A., et al., "Primary Structure of a Human Small Nuclear Ribonucleoprotein Polypeptide as Deduced by cDNA Analysis", *Journal of Biological Chemistry,* 264(9):5024–5030 (1989).

Scofield, et al., "60 kD Ro/SSA Autoepitopes are Found in Regions of Homology Between Ro/SSA and the Nucleocapsid Protein of Vesicular Stomatis Virus", *Arthritis and Rheumatism,* 33(9):S101, (1990).

Scofield, et al., "The Autoantigenicity of Human 60kD Ro/SSA is Related to Homologies Between Ro/SSA and the Nucleocapsid Protein of Vesicular Stomatis Virus", *Clinical Research,* 38(2):316A, (1990).

Sharpe, N.G., et al., "Isolation of cDNA Clones Encoding the Human Sm B/B' Autoimmune Antigen and Specifically Reacting with Human Anti–Sm Autoimmune Sear", *FEBS Letters,* 250(2):585–590 (1989).

Sillekens, P.T.G., et al., "cDNA Cloning of the Human U1 snRNA–Associated A Protein: Extensive Homology Between U1 and U2 snRNP–Specific Proteins", *EMBO Journal,* 6(12):3841–3848 (1987).

Sturgess, A.D., et al., "Characteristics and Epitope Mapping of a Cloned Human Autoantigen La", *Journal of Immunology,* 140(9):3212–3218 (1988).

Harlow et al. "Antibodies: A Laboratory Manual", Cold Spring Harbor Laboratory, 1988.*

Miller et al PNAS 87: 9933, 1990.*

Wista et al *Molecular Biology of the Gene*: 836, 1990.*

Reuter et al PNAS 83: 8689, 1986.*

Robeard et al JBC 264(9): 5024, 1989.*

Deutscher et al PNAS 85: 9479, 1988.*

* cited by examiner

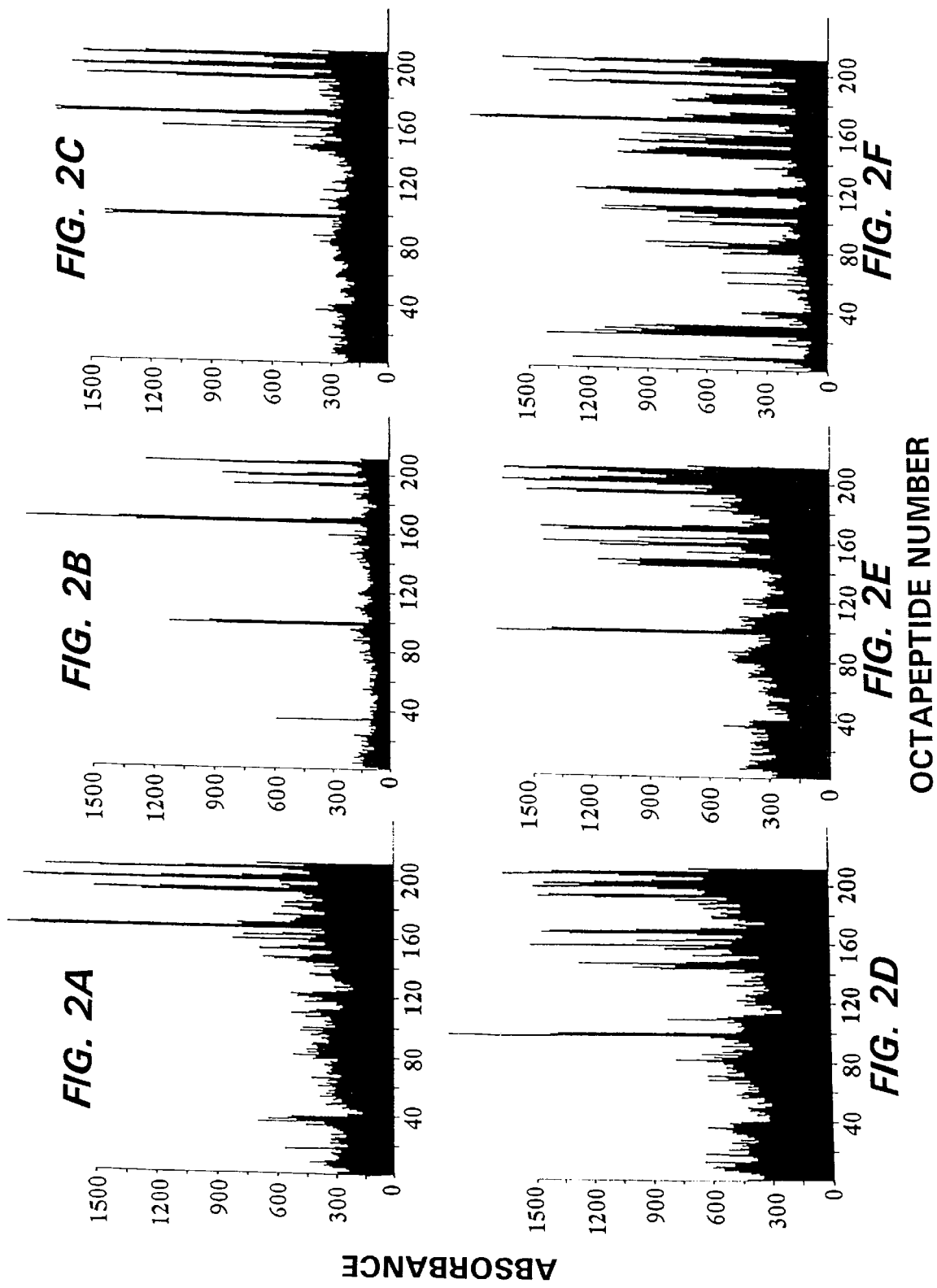

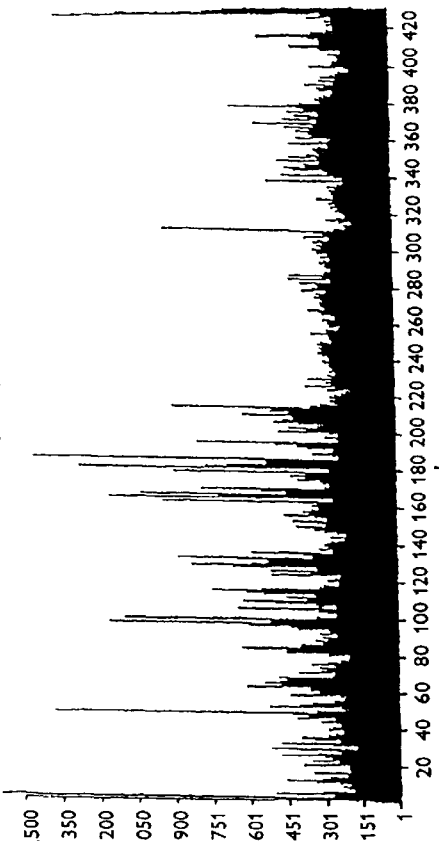
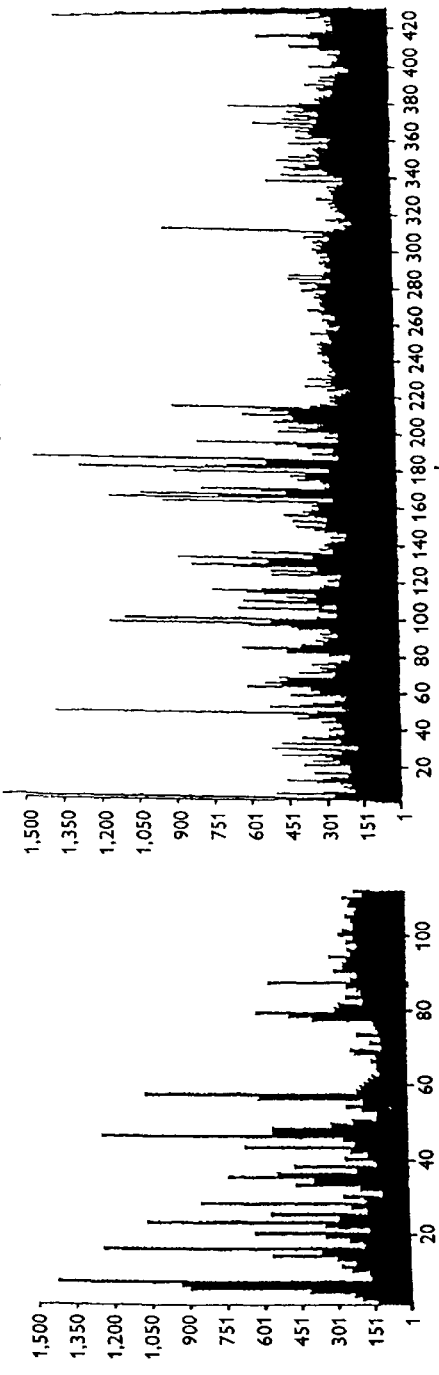
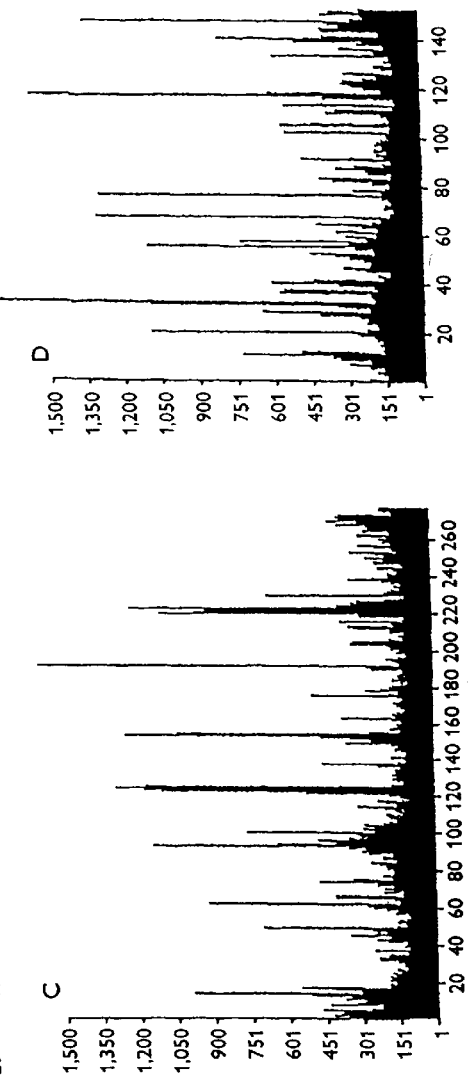
FIG. 6A  FIG. 6B  FIG. 6C  FIG. 6D
OCTAPEPTIDE NUMBER
ABSORBANCE

NON-HUMAN ANIMAL MODEL FOR SYSTEMIC LUPUS ERYTHEMATOSIS

This is a continuation-in-part of U.S. Ser. No. 07/867,819 filed Apr. 13, 1992 by John B. Harley (now abandoned), which is a continuation-in-part of U.S. Ser. No. 07/648,205 filed Jan. 31, 1991 by John B. Harley for "Assays and Treatments for Autoimmune Diseases" (now abandoned), which is a continuation-in-part of U.S. Ser. No. 07/472,947 entitled "Assays and Treatments for Autoimmune Diseases" filed Jan. 31, 1990 by John B. Harley, now abandoned; the teachings of which are specifically incorporated herein.

The United States government has rights in this invention by virtue of grants from the National Institutes of Health AR39577, AI24717, AI21568, AI31584 and AR01844, and the U.S. Department of Veterans Affairs.

BACKGROUND OF THE INVENTION

This invention is in the field of etiological agents and induction mechanisms of autoimmunity, and specifically is a method of making an animal model for autoimmune disease.

General Discussion of Autoimmunity and Autoimmune Diseases

Autoimmunity is described as an immune response mounted against self-components which ultimately results in pathogenic consequences. Diseases which result from autoimmune responses are widespread and varied in clinical presentation. One common factor shared by many of these disease entities is the lack of a known etiologic agent or triggering event for the production of these aberrant responses.

As used herein, autoimmune diseases are diseases that are primarily autoimmune, as well as diseases which do not appear to be primarily autoimmune but have immune manifestations involving immunoglobulins, antigen specific B cell surface receptors, or antigen-specific T cell receptors. Examples of diseases which fall into these categories are systemic lupus erythematosus, Sjögren's syndrome, rheumatoid arthritis, juvenile onset diabetes mellitus, Wegener's granulomatosis, inflammatory bowel disease, polymyositis, dermatomyositis, multiple endocrine failure, Schmidt's syndrome, autoimmune uveitis, Addison's disease, adrenalitis, Graves Disease, thyroiditis, Hashimoto's thyroiditis, autoimmune thyroid disease, pernicious anemia, gastric atrophy, chronic hepatitis, lupoid hepatitis, atherosclerosis, presenile dementia, demyelating diseases, multiple sclerosis, sub acute cutaneous lupus erythematosus, hypoparathyroidism, Dressler's syndrome, myasthenia gravis, autoimmune thrombocytopenia, idiopathic thrombocytopenic purpura, hemolytic anemia, pemphigus vulgaris, pemphigus, dermatitis herpetiformis, alopcia aerata, pemphigoid, scleroderma, progressive systemic sclerosis, CREST syndrome (calcinosis, Raynaud's phenomenon, esophageal dysmotility, sclerodactyly, and telangtasia), adult onset diabetes mellitus (Type II diabetes), male and female autoimmune infertility, ankylosing spondolytis, ulcerative colitis, Crohn's disease, mixed connective tissue disease, polyarteritis nodosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipidsyndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leshmaniasis, trypanosomiasis, Takayasu's arteritis, polymyalgia rheumatica, temporal arteritis, shistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, glomerulonephritis, graft versus host disease, transplantation rejection, human immunodeficiency virus infection, echovirus infection, cardiomyopathy, Alzheimer's disease, parvovirus infection, rubella virus infection, Hodgkin's and Non-Hodgkin's lymphoma, renal cell carcinoma, multiple myeloma, Eaton-Lambert syndrome, relapsing polychondritis, malignant melanoma cryoglobulinemia, Waldenstrom's macroglobulemia, Epstein-Barr virus infection, mumps, amyotrophic lateral sclerosis, stiff man syndrome and autoimmune gonadal failure. Immunization is any procedure leading to a humoral or cellular immune response to a specific substance. An autoantigen is any protein, or portion of a protein, specifically recognized by and bound to an auto antibody. An etiologic or antigenic agent is any agent eliciting production of autoantibodies, including infectious agents such as bacteria, viruses, viroids, Rickettsia, and fungi, or environmental agents, including foods or chemicals. These agents can be protein, portions of protein, or portion of a protein in combination with a polysaccharide. An auto antibody is any immunoglobulin, antigen specific B cell surface receptor (surface immunoglobulin), or antigen specific T cell receptor binding to or immunoreactive with a self-protein or any portion of a self-protein.

Autoimmune Rheumatic Diseases

Rheumatologis illnesses encompass a large number and wide spectrum of different autoimmune diseases, such as rheumatoid arthritis, scleroderma, dermatomyositis, polymyositis, discoid lupus erythematosus, Sjogren's syndrome and systemic lupus erythematosus. For the most part, the etiologies and pathogenic mechanisms of these disorders are still unknown. One common theme in many of these maladies is the presence of substantial quantities of antibodies immunoreactive with self-components. One example of such a rheumatic disease is systemic lupus erythematosus.

Systemic Lupus Erythematosus: Prevalence, Debilitation, Diagnosis, Clinical Manifestations and Serological Findings Systemic lupus erythematosus affects at least 100,000, and perhaps up to 500,000 people, in the United States. It is estimated that one in 1000 American Caucasian women between the ages of 14 and 65 have systemic lupus erythematosus, as are up to four of every 1000 American black women in the same age group (Harley, et al., *Rheum. Dis. Clin. North Amer.* 14:13–56, 1988). Most of these patients have significant morbidity and mortality resulting from both the substantial major organ involvement from this disease process and from the harsh therapeutic interventions implemented in the treatment of this poorly understood clinical entity.

Due to the varied clinical presentations associated with systemic lupus erythematosus, guidelines were revised in 1982 to aid in its diagnosis (Tan, et al., *Arthritis Rheum.* 25:1271–1277, 1982). Eleven clinical criteria were proposed, four of which must be present to classify a patient as having systemic lupus erythematosus. These criteria include a malar rash; discoid rash; photosensitivity; oral ulcers; arthritis; serositis manifest by pleuritis or pericarditis; nephritis manifest by proteinuria or cellular casts; central nervous system involvement manifest by seizures or psychosis; hematologic involvement manifest by hemolytic anemia, leukopenia, lymphopenia or thrombocytopenia; immunologic involvement manifest by LE cells, biologically false positive serologic test for syphilis or anti-Sm antibodies; anti-native DNA antibodies and anti-nuclear antibodies.

One characteristic shared by many of these patients is the presence of high titers of autoantibodies in their sera. These autoantibodies may be directed against a myriad of host components, such as ribonucleoproteins (Sm, nRNP, Ro and La), DNA, RNA, histones, erythrocytes, and immunoglobulin, as well as other characterized and uncharacterized autoantigens.

Autoantibodies and Autoantigens in Systemic Lupus Erythematosus, Associations with Clinical Manifestations and Disease Prognosis The near universal presence of autoantibodies is the most convincing data that leads to the general conclusion that lupus is an autoimmune disease. Autoantibodies are found in the serum of the vast majority of patients. Indeed, a positive antinuclear antibody is present in over 98% of lupus patient sera when human tissue culture cells are used as substrates for the test. This result means that patients make an autoantibody that binds a constituent of self which is contained in these cells. Many, perhaps more than 50, different constituents of self or autoantigens, are known to be bound by lupus autoantibodies (Harley, et al., *Rheum. Dis. Clin. North Amer.* 14:13–56, 1988). In most situations these autoantibodies are present in low concentrations. There are a few autoantibody systems that are present in extraordinarily high concentrations, often exceeding 1 mg/ml (Maddison, et al., *Arthritis Rheum.* 20:819–824, 1977; Gaither, et al., *Protides Biol. Fluids Proc. Colloq.* 33:413–416, 1985; Harley, et al., *Arthritis Rheum.* 29:196–206, 1986). Such incredible amounts of autoantibody are typically directed against the RNA-protein autoantigens known as Sm, nRNP, La and Ro.

Nuclear ribonuclear protein (nRNP) and Sm are subsets of proteins associated with U small nuclear RNP particles. These complexes function as the spliceosome and excise introns from heteronuclear RNA. Anti-nRNP immunoprecipitates only the U1 RNA. Most commonly these sera bind a peptide known as the 70K peptide, but others also bind the A and/or C peptides which are also unique to U1. About 40% of lupus sera have the anti-nRNP precipitin (Harley, et al., *Rheum. Dis. Clin. North Amer.* 14:13–56, 1988). Mattioli and Reichlin first described anti-nRNP as well as its partial, but distinct, antigenic relationship with anti-Sm (Mattioli, et al., *J. Immunol.* 110:1318–1324, 1973) which had been described earlier by Tan and Kunkel (Tan, et al., *J. Immunol.* 96:464–471, 1966). Specific clinical manifestations have also been associated with the presence of anti-nRNP autoantibodies including Raynaud's phenomenon, myositis and sclerodactyly (Munves, et al., *Arthritis Rheum.* 26:848–853, 1983). Also, a better overall prognosis and less severe nephritis has been found in patients whose sera only precipitate the nRNP antigen (Reichlin, et al., *Clin. Exp. Immunol.* 83–286–290, 1991).

Anti-Sm immunoprecipitates U1, U2, U4/U6 and U5 RNAs. The particles containing these RNAs all contain the B or B' and D autoantigenic peptides. Anti-Sm virtually always binds to the B/B' peptides at 28 kD in immunoblot, with most also binding the smaller D peptide. Anti-Sm is the only anti-RNA-protein autoantibody system which is argued to be specific for lupus, though there are those who disagree (Munves, et al., *Arthritis Rheum.* 26:848–853, 1983). Indeed, anti-Sm is the only RNA-protein autoantibody precipitin whose presence is one of the criteria for classification of systemic lupus erythematosus (Tan, et al., *Arthritis Rheum.* 25:1271–1277, 1982). Anti-Sm has been associated with nephritis and isolated central nervous system involvement (Munves, et al., *Arthritis Rheum.* 26:848–853, 1983; Maddison, et al., *Arthritis Rheum.* 20:819–824, 1977; Winfield, et al., *Arthritis Rheum.* 21:289–294, 1978).

Due to the important role of these proteins in the process of heteronuclear RNA processing, the conservation of the sequences of these proteins throughout evolution is not unexpected. Sm B and Sm D proteins are found in humans (Hinterberger, et al., *J. Biol. Chem.* 258:2604–2613, 1983; Matter, et al. *Arthritis Rheum.* 25:1278–1283, 1982), rodents (Hinterberger, et al., *J. Biol. Chem.* 258:2604–2613, 1983; Lerner, et al. *Nature* 283:220–224, 1980), Xenopus (Fritz, et al. *J. Mol. Biol.* 178:273–285, 1984; Zeller, et al. *Cell* 32:425–434, 1983), and Drosophila (Craft, et al. *Mol. Biol. Rep.* 15:159, 1991). The Sm N protein is also found in humans and is homologous to the Sm B proteins (Schmauss, et al., *Nucleic Acids Res.* 17:1733 (1989)). Proteins which are immunologically reactive with anti-Sm autoantibodies and are of a similar size to human Sm B and Sm D are found in plants (Palfi, et al. *Nucleic Acids Res.* 17:1445–1458, 1989). In addition, recent sequence data from Griffin, et al. find 99% sequence homology between human Sm B, rat Sm B and Drosophila Sm B (Craft, et al. *Mol. Biol. Rep.* 15:159, 1991).

Other antibodies directed against RNA-protein complexes associated with systemic lupus erythematosus are anti-Ro and anti-La. These antibodies are present in 30–50% and 15% of lupus patients, respectively. Anti-Ro and anti-La autoantibodies are also present in other rheumatic diseases, such as Sjogren's syndrome and mothers of children with congenital complete heart block. Other common autoantibodies associated with lupus are those directed against histones, cardiolipin, rheumatoid factor, ribosomal P proteins and single stranded and double stranded DNA.

Induction of Autoimmunity and Autoimmune Diseases

Several autoimmune diseases have been experimentally induced in genetically predisposed animal models. These models have characteristic immune responses and clinical manifestations which mimic the human disease. This summary briefly discusses three examples of such induced autoimmune responses.

Thyroiditis

Induction of human chronic thyroiditis in rabbits by injection of thyroglobulin by Rose and colleagues is a classic example of an induced immune response against a native protein (Witebsky, et al., *J. Am. Med. Assoc.* 164:1439–1447, 1957). The best antibody responses to thyroglobulin were mounted in rabbits immunized with thyroglobulin in Freund's Complete Adjuvant or by altered thyroglobulin without Freund's Complete Adjuvant (Rose, et al., *Ann. N.Y. Acad. Sci.* 124:201–108, 1965). Antibodies to thyroglobulin have been induced in many different animal species by thyroglobulin immunization ((Witebsky, et al., *J.*

Am. Med. Assoc. 164:1439–1447, 1957; Rose, et al., *Ann. NY Acad. Sci.* 124:201–108, 1965). Different responsiveness of various strains of inbred mice to thyroglobulin has been detected (Esquivel, et al., *J. Exp. Med.* 145:1250–1263, 1977). This has led to the investigation of the genetic control of thyroid autoimmunity (Esquivel, et al., *J. Exp. Med.* 145:1250–1263, 1977; Rose, et al., Talal N. ed. *Autoimmunology Genetic, Immunologic Virologic. and Clinical Aspects.* New York: Academic Press, 63–87, 1977; Rose, et al., *Immunol. Reviews* 55:229–314, 1981).

Experimental Allergic Encephalomyelitis

Experimental allergic encephalomyelitis is another immunization induced autoimmune disease. In this model the T-cell component appears to be the most important and is the best characterized. In mice this disease is induced by immunization of myelin basic protein with pertussis toxin. The T-cell response in this disease is initially directed against a short peptide, termed Ac1-11 (Lehmann, et al., *Nature* 358:155–157, 1992). Additional regions of myelin basic protein become targets of T-cell responses in chronic disease. Lehmann et al. have immunized susceptible mice with the initial T cell target peptide, Ac1-11, in combination with pertussis toxin and established experimental allergic encephalomyositis along with T cell responses to three additional regions of myelin basic protein (Lehmann, et al., *Nature* 356:155–157, 1992). B cells are not thought to play a major role in this autoimmune disease; therefore, no immunoglobulin studies have been reported.

Myasthenia Gravis

Myasthenia gravis is caused by autoantibodies to the nicotine acetylcholine receptor. Animals immunized with acetylcholine receptors develop myasthenia gravis symptoms. T and B cell epitopes of this receptor are recognized after immunization with the acetylcholine receptor in animal models. The immune responses bear important similarities to those found in human patients (Manfredi, et al., *J. Lab. Clin. Med.* 120:13–21, 1992; Tzartos, et al., *Autoimmunity* 8:259–270, 1991).

Systemic Lupus Erythematosus (SLE)

A proposed model of SLE has been reported by Shoenfeld, et al., in which animals were immunized With a peptide derived from a self-component which produced a clinical syndrome associated with autoimmunity against the self-component. This was believed to be the first report of an immunization-induced model of systemic lupus erythematosus.

Similar binding regions of SM and nRNP proteins are detected in these mouse and rabbit peptide-induced models as are present in human systemic lupus erythematosus patient sera. The development pattern of the additional immunoglobulin binding regions to the spliceosomal autoantigens are almost identical between the peptide-induced model and human disease. In addition, the animals which develop this peptide-induced lupus autoimmunity which mimics human disease also eventually develop many of the same clinical manifestations of the human disease of systemic lupus erythematosus. This animal model provides an opportunity to describe a mechanism of anti-spliceosomal autoimmunity, the process by which this autoimmune response is initiated, the association of this immune response to clinical symptomatology and the potential etiological agent(s) and therapeutic intervention(s) for human systemic lupus erythematosus.

It is, therefore, an object of the present invention to provide diagnostic and therapeutic agents for autoimmune disorders, and methods of use thereof.

It is a further object of the present invention to provide a mechanism for the development of autoimmune disorders including systemic lupus erythematosus and related disorders which allows the development of new diagnostics and therapeutic agents for the treatment of these autoimmune disorders.

It is a further object of the present invention to provide animal models of systemic lupus erythematosus and other autoimmune diseases for the evaluation of diagnostics and of therapeutic agents.

It is a further object of the present invention to provide animal models of systemic lupus erythematosus and other autoimmune diseases for the generation of immunologic reagents.

SUMMARY OF THE INVENTION

A specific method has been developed to produce an autoimmune response and resulting clinical symptoms for a particular disease process. Peptides or immunoreactive structures formed by peptides (jointly referred to herein as "peptides") derived from an autoantigen and which are bound by autoantibody or T cell receptors are identified. These peptides or other structures may represent an early or initial component of an autoantibody response. These peptides are then used to induce an immune response. It has been discovered that immunization with only a single epitope can induce a polyclonal autoimmune response. This initial immune response evolves into an autoimmune response directed against the other portions of the protein from which the peptide was derived, as well as other proteins and in some cases nucleic acid. Subsequently, clinical manifestations may appear that are also found in the clinical illness.

In the case of the autoimmune response against the lupus Sm autoantigen, PPPGMRPP (Sequence ID No.1) and PPP-GIRGP (Sequence ID No.2) are presumed to be the earliest peptides bound by some patients with human anti-Sm. After immunization of animals with these peptides, an autoimmune response develops against the spliceosome and its components which is then followed by the clinical manifestations of disease and pathogenic consequences of the induced autoimmune process, which in many aspects mimic the clinical symptoms recognized as characteristic of the related human autoimmune disease.

The generation of anti-Ro autoimmunity in animals has also been achieved by immunization with the autoantigenic peptides containing the sequences, CAIALREYRKKM-DIPA (Sequence ID No.3) and QEMPLTALLRNLGKMTC (Sequence ID No.4), from the 60 kD Ro/SSA autoantigen.

Once the peptides are known that are capable of inducing autoimmunity against the component of self from which they are derived (or autoantigen) and potentially of inducing autoimmune disease, the possibility of testing for autoimmune disease by screening for antibodies or T cell responses to these, induction peptides is feasible. The animal model of induced systemic lupus erythematosus should be useful in testing the efficacy of various diagnostics as well as of various medications or immune modulation therapies, which could lead to more optimal medical management, attenuating autoantibody production or the relief of clinical manifestations. In addition, the animal model has the capacity to be the origin of many useful reagents including antisera and individual immunoglobulin. For example, recombinant DNA techniques could be used to develop monoclonal autoantibodies of defined specificities.

BRIEF DESCRIPTION OF THE DRAWINGS

FIGS. 2A, 2B, 2C, 2D, 2E, and 2F display the expansion of the octapeptide binding pattern over time from the sera of one anti-Sm and anti-nRNP precipitin positive patient. This anti-Sm and anti-nRNP precipitin positive patient shows an increase in the number of antigenic determinants over time. Panel 2A (Apr. 1, 1986), Panel 2B (Jul. 7, 1987), Panel 2C (Jan. 1, 1988), Panel 2D (Jun. 6, 1988), Panel 2E (Oct. 10, 1988), and Panel 2F (Dec. 12, 1988) span a two and a half year progression of systemic lupus erythematosus and exhibit an increase from binding four groups of octapeptides to recognizing fifteen groups of peptides.

FIGS. 6A, 6B, 6C, and 6D are a representation of the antibody binding regions of one PPPGIRGP immunized rabbit serum with the overlapping octapeptides of Sm and nRNP antigenic proteins which do not contain the peptide of immunization. After twenty weeks into the immunization protocol, sera from rabbit GIR2 binds many different regions of Sm D (Panel 6A), nRNP 70K (Panel 6B), nRNP A (Panel 6C), and nRNP C (Panel 6D). Preimmunization serum does not bind any of the octapeptides above background.

DETAILED DESCRIPTION OF THE INVENTION

Figure 1:
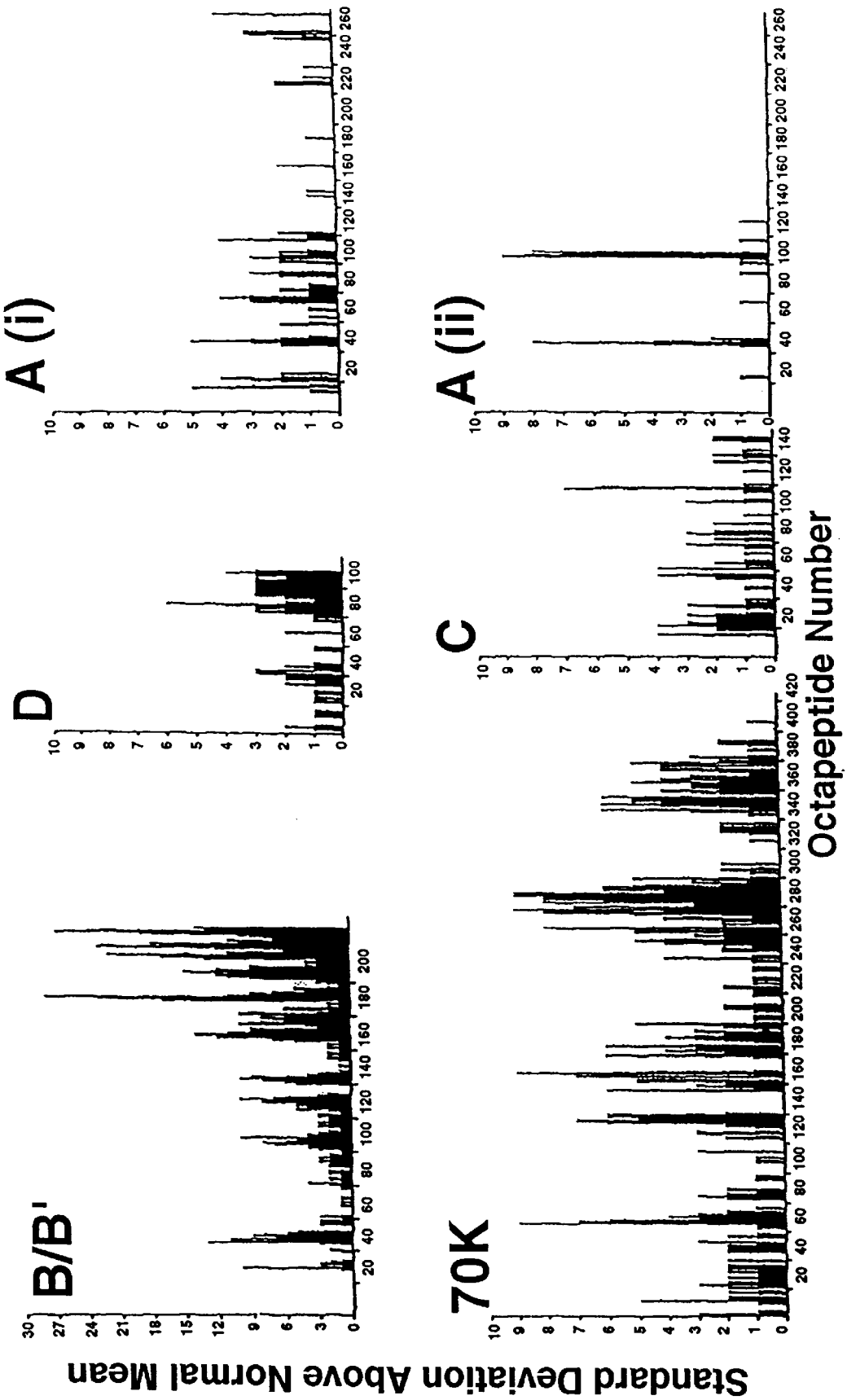
FIG. 1 presents the average binding of anti-Sm or anti-nRNP sera with the overlapping octapeptides of the Sm B/B', Sm D, nRNP 70K, nRNP A, and nRNP C proteins. Binding is expressed as standard deviations above the average normal sera binding for each protein. A(i) and A(ii) are the two patterns of nRNP A binding.
Figure 3A:
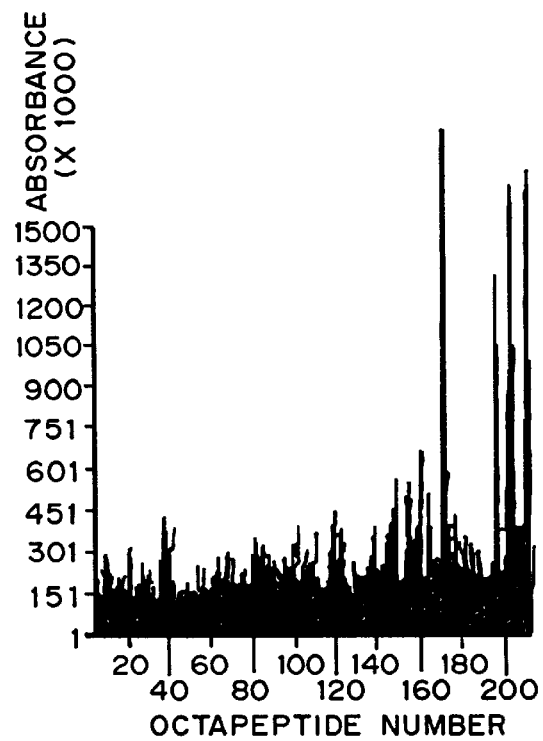
FIGS. 3A, 3B, 3C and 3D are a comparison of human lupus patient sera reactivity to peptide-immunized rabbit sera binding of Sm B/B' octapeptides. Panels 3A and 3C present the antigenic regions of two individual lupus patient sera. Panels 3B and 3D display the octapeptides bound by two peptide-immunized rabbits, GIR1 and GMR2, at week 10 after first immunization with PPPGIRGP (Sequence ID No.2) or PPPGMRPP (Sequence ID No.1), respectively.
Figure 3B:
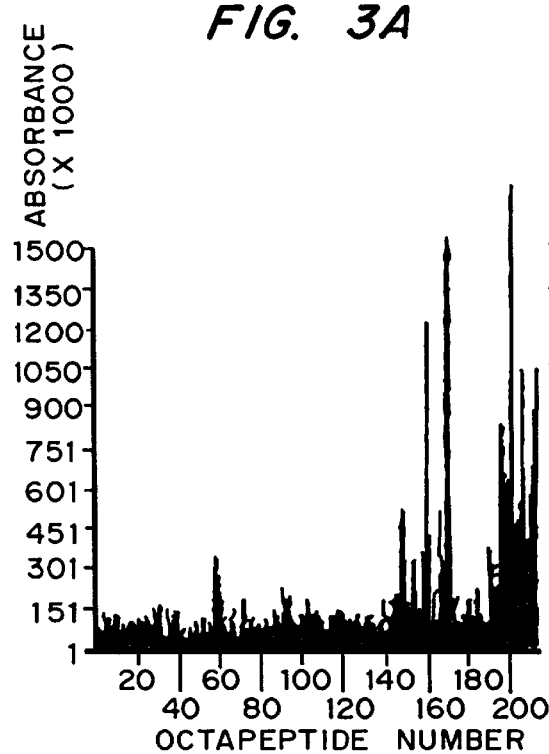
Figure 3C:
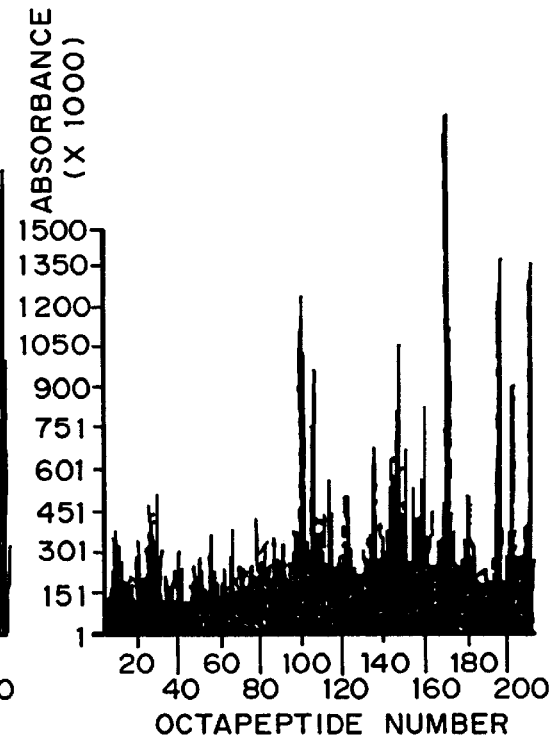
Figure 3D:
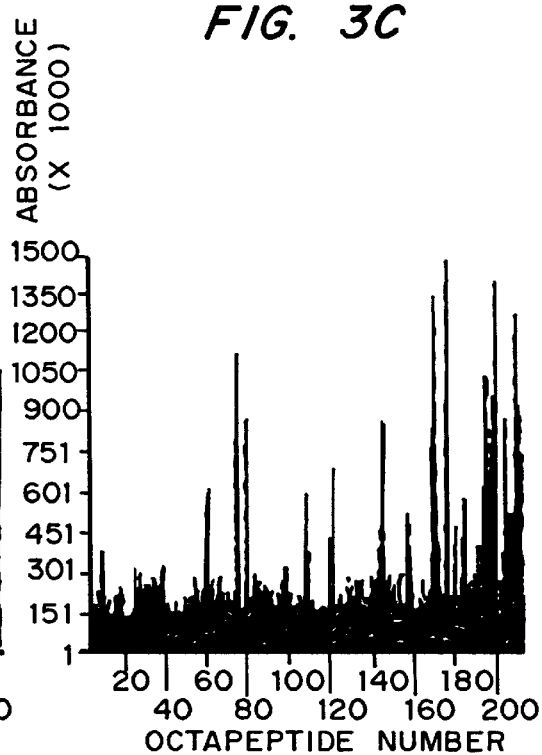

A procedure which generates high levels of autoantibodies, such as anti-Sm and anti-nRNP (anti-spliceosome) autoantibodies in normal experimental animals has been developed. Anti-Sm and anti-nRNP are commonly found at extraordinary concentrations in the sera of lupus patients. The Sm and nRNP autoantigens have been identified as components of the spliceosome complex which provides cells with the capacity to remove introns from heteronuclear RNA. The anti-Sm portion of this anti-spliceosome response is thought by many to be especially specific for lupus patients. Animals are immunized with selected short peptides from the autoantigens, for example, the proteins that constitute Sm and nRNP. The selected peptides are those that are bound by human autoantibodies from lupus patients. With additional boosting after developing an immune response to the short peptide, the animal develops a fully mature humoral autoimmune response to the spliceosome (Sm and/or nRNP proteins). Indeed, as many as 61 different peptide epitopes of the spliceosome complex have been bound by an individual rabbit serum. In addition, some animals have made precipitating levels of autoantibodies which are demonstrable in double immunodiffusion assays.

The model of peptide-induced spliceosomal autoantibodies is distinct because it involves immunization with a peptide derived from a self-component and produces a clinical syndrome associated with autoimmunity against the self-component; it results in an anti-peptide response that develops into anti-self-component autoimmunity; and it is the first immunization-induced model of systemic lupus erythematosus. Similar binding regions of Sm and nRNP proteins are detected in these mouse and rabbit peptide-induced models as are present in human systemic lupus erythematosus patient sera. The development pattern of the additional immunoglobulin binding regions to the spliceosomal autoantigens are very similar when sera from the peptide-induced model and the human disease are compared. In addition, the animals which develop this peptide-induced lupus autoimmunity which mimics the human disease also eventually develop many of the same clinical manifestations of the human disease of systemic lupus erythematosus.

Sera or a different source of antibody or T cell receptors is screened using overlapping octapeptides of the autoantigens of interest. Peptides which are recognized by these patient sera collected early in disease are tested for their ability to induce the expanded immune response against whole autoantigen. The identified sequences are bound by greater than two standard deviations above the mean of the control sera (normal and patient sera with no anti-Ro precipitins). These identified initial peptides are used to immunize animals. After peptide immunization antibodies are produced in the immunized animals which bind not only the immunization peptide but also other regions of the protein from which the immunization peptide was derived. This induced autoimmune response eventually expands to produce antibodies which bind other associated autoantigens.

This general method can be used to develop autoimmunity against any of a large number of now known and to be discovered autoantigens.

It is important to place the anti-peptide responses in the context of autoimmunity. A basic assumption is that there is a selection of peptides from a component of self that is an antigen in an autoimmune or presumed to be autoimmune disease. The induction of an immune response against some of these peptides will induce an immune response against the component of self from which the peptide had been derived. Antipeptide responses that do not in some way lead to the immune identification, utilization or processing of the self-component from which it had been derived are not autoimmune. The constituent structures of self-components other than peptides are considered in an analogous fashion.

A number of peptides, preferably consisting of eight amino acids, are disclosed that are bound by human autoantibodies characteristic of SLE and other autoimmune disorders. The peptides are made synthetically, based on the published amino acid sequences for known autoantigens, Ro/SSA, La/SSB, nRNP, and Sm B/B'. They have a variety of uses, for example, as components in diagnostic assays, potentially as therapeutics, and in research on the possible causes of these autoimmune diseases.

Definition of Linear Epitopes and Methods of Synthesis

As used herein, a peptide is defined as consisting of less than one hundred amino acids and will generally be an octapeptide. Peptides of up to forty amino acids, more preferably of between four and twenty-five amino acids, most preferably eight amino acids, can be synthesized using any one of the methods known to those skilled in the art. In general, an epitope of a protein is composed of between two and eight amino acids (see Watson et al., "Certain Properties Make Substances Antigenic," in *Molecular Biology of the Gene*, Fourth Edition, page 836, paragraph 3, (The Benjamin/Cummings Publishing Company, Menlo Park, 1987, Appll, et al., *J. Immunol.* 144,976-983(1990). A preferred method is described in the detail in the examples. The octapeptides described in the examples herein are derived from published sequences encoding the autoantigens. The number in parenthesis is the position in the sequence for the first amino acid residue of the first octapeptide that binds. As used herein, the peptides can contain the entire native epitope, or portions thereof sufficient to react with autoantibody.

Although described with reference to specific sequences, a number of substitutions using natural or synthetic amino acids can be made in the peptides to yield an peptide acting as a linear epitope that is functionally equivalent to the disclosed sequence, for example, as demonstrated by James and Harley, *J. Immunology* 148:2074–2079 (April 1992). Accordingly, the term linear epitope as defined by a specific sequence is used herein to include peptides having substitutions yielding a peptide bound in an equivalent manner or extent by an antibody or autoantibody. For example, using monoclonal antibodies against peptide determinants of Sm B/B', substitution studies demonstrated that A, G, and S can substitute for R in PPPGMRPP (Sequence ID No.1) in the binding of one antibody, KSm3. Analogously, F, H, T, V and Y can substitute for I in PPPGIRGP (Sequence ID No.2) in the binding of KSm3.

Screening of Peptides by Binding to Autoantibodies

Solid phase binding of autoantibodies to peptides has proven useful for examining sequential linear epitopes and defining important residues in epitope structure but is expected to be less useful in defining conformational epitopes or regions where two or more linear, but not sequential, epitopes are brought together by the tertiary structure. In addition, although many peptides will tend to assume conformations in solution that are not found in the native protein structure, true epitopes may still be delineated by this method. Those peptides that tend to have a structure similar to that found in the native molecule are expected to usually be bound by a larger proportion of the autoantibodies that bind the analogous sequence on the native protein and may even be bound with greater affinity.

The examples below describe in detail how the peptides can be synthesized and screened for binding.

Use of Peptides in Treatment and Classification of Patients

Diagnostics.

It is expected that naturally arising human lupus follows a progression similar to that induced in the rabbits. Using this model, an immune response to a peptide, perhaps induced by some substance other than the autoantigen from which the peptide has been derived, is the seminal, initiating event for the subsequent autoimmunity and disease manifestations, where they occur. It is also expected that many other autoimmune diseases follow the same general progression.

A structure, such as a peptide, that is capable of inducing autoimmunity is not necessarily identical to the structure found in the autoantigen. Indeed, it is possible that these structures would commonly be at least slightly different, when comparing the substance that induces the autoimmune response and the analogous structure in the autoantigen. On the other hand, there must be a basis for the non-autoantigen substance to induce autoimmunity. This is best identified as a cross-reaction wherein the immune recognition molecule binds, though not necessarily equally, to both the non-autoantigen substance as well as to the autoantigen. Whether a stage of this process exists in which both peptides, i.e., peptide derived from the non-autoantigen as well as the autoantigen, are individually processed and recognized by the immune system is not known.

Figure 9:
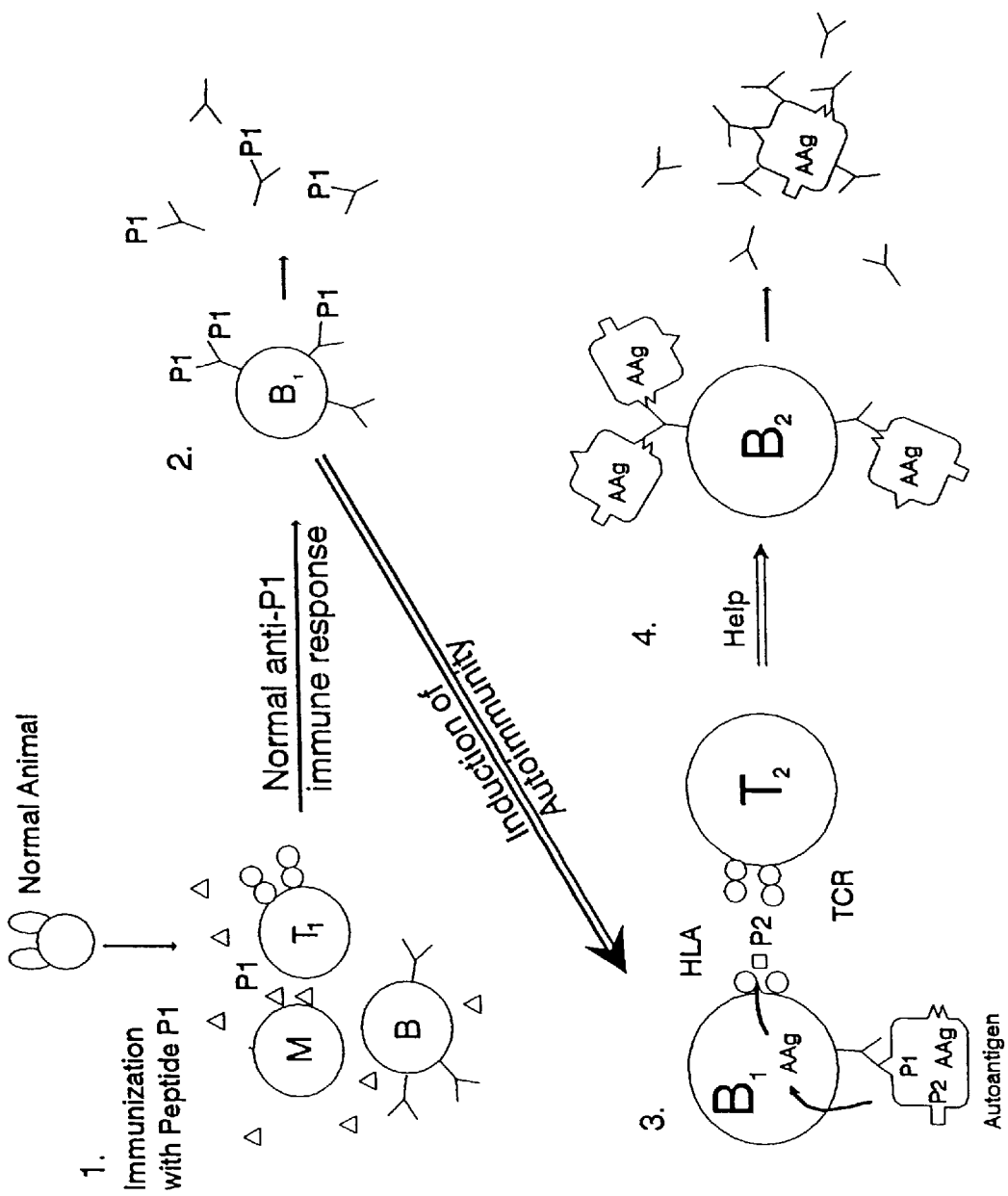
FIG. 9 presents a proposed model for the induction of autoimmunity in the animals immunized with autoantigenic peptides and which may operate in human lupus and other autoimmune diseases. Step 1. A normal animal is immunized with an autoantigenic component, such as a peptide (P1) from an autoantigen (AAg). Step 2. An immune response against this component is generated. Step 3. Some of the B cells ($B_2$) which make antibody against this component also bind the surface of the autoantigen. Alternatively, the component of the anti-P1 antibody which is also capable of binding autoantigen binds the Fc receptor of antigen processing cells. In either case, the antigen is internalized and other constituent peptides (P2, for example) are presented on Class II HLA molecules of the antigen presenting cells ($B_2$ or M) to T cell receptors on T cells ($T_2$). Step 4. These T cells are capable of providing help to these and other B cells ($B_2$ and $B_3$) which then bind other structures on the surface of the autoantigen.

The proposed mechanism for how the progression of the immune response may occur is shown in FIG. 9. An immune response against a non-autoantigenic substance occurs. Some fraction of the antibodies thereby produced recognize the autoantigen and hence are autoantibodies. These autoantibodies facilitate the processing and antigen presentation of the autoantigen via the B cell surface immunoglobulin which serve as receptors, in this case for autoantigen, or via immunoglobulin cell surface receptors that are found on a variety of cells capable of antigen presentation. Once this occurs the immune response expands to other structures of the autoantigen and a full-blown, complete autoimmune response against the autoantigen ensues, which can result in clinical illness.

The mechanism proposed is that autoimmune responses progress from one or a few initial antigenic structure(s) to a much more complex response focused upon the autoantigen. Elucidating the pattern of progression and understanding the relationship of autoimmune serologic findings to clinical manifestations places the physician in a strong position to accurately prognosticate and prepare patients and their families for the more likely outcomes.

In the case of systemic lupus erythematosus and the anti-Sm response, one method is to repeat the assays determining autoantibody binding to peptides over time. The effect of the peptide in vitro on cells from patients can also be measured. Proliferation, secretion of cytokines, interferons and other substances, expression of cell surface molecules and activation are typically useful diagnostic indicators.

Production of Reagents

This strategy to generate autoimmunity can also be used to develop reagents that would be useful in diagnosis or treatment of autoimmune disorders. Animal antibodies that compete with or otherwise facilitate the identification of particular fine specificities of binding can be important in evaluating prognosis. Moreover, the peptide binding pattern to the octapeptides from the nRNP A protein show two different patterns. It should be possible to correlate a particular pattern found in a patient to obtain an indication of the stage the disease currently is at as well as the clinical prognosis. Reagents developed as a consequence of immunizing animals with autoantigenic peptides could be used to identify these differences. Such reagents include antisera, T cell lines, subsets of antibodies, individual antibodies, subsets of cells bearing a subset of the T cell receptors, individual T cell receptors, and cytokines and other substances elaborated by cells from the animal. The antibodies and T cell receptors are construed to include recombinant antibodies or T cell receptors derived from a peptide-immunized animal.

The RNA-protein particles which are the major autoantigens may now be purchased commercially. The reagents made available by the animal model of autoimmunity described herein will be useful in the manufacturing and testing of autoantigens. Affinity purification using animal antiserum (absorbed or otherwise prepared) could be used for purification of the naturally occurring autoantigens.

Therapeutics.

Having a theory for the mechanism of disease provides the opportunity to apply new strategies for prevention of disease and for specific immunologic correction of the immune abnormalities that lead to disease, and therefore more accurately design the therapy.

For example, with the realization that the generation of autoimmune disease can be divided into phases comes the appreciation that the therapeutic opportunities will be similarly partitioned. As a specific example, the influence of vaccination with an analog of PPPGMRPP (Sequence ID No.1) will be different depending not only upon the structure of the immunogen, but also upon the pharmaceutical carrier, upon the maturity of the autoimmune response against PPPGMRPP (Sequence ID No.1) and Sm, and upon other therapeutics that may be administered concomitantly. Such therapeutics include drugs as well as biologics, such as cytokines, immunogloblins, and interferons, among others.

An individual identified at risk for the development of an autoimmune disease, but who does not yet manifest autoimmunity or symptoms of the disease, may require a special therapeutic approach. This is an opportunity to induce immune suppression before the process leading to autoimmune disease is initiated. Strategies such as intravenous administration of large amount of the initiating structure is known to induce tolerance. Small sub-immunogenic doses of the initial immunogen can also be used to induce tolerance.

There is a limited opportunity to interrupt or redirect an immune response that has been initiated against the first components of the autoantigen. Here again the induction of suppression by the use of the component peptides or analogs thereof with or without concomitant drugs or biologics has the potential to inhibit progression into an autoimmune disorder. Once autoimmunity against the autoantigen is established, the use of component peptides or their analogs with or without concomitant drugs or biologics may interrupt the course of the autoimmune response, thereby ameliorating the illness.

The animal model provides an opportunity to discover ways of interrupting and reversing the autoimmune process. For example, it has been observed that one of the rabbits immunized with Map™-PPPGMRPP (Sequence ID No.1) seemed to improve clinically somewhat after developing the most severe manifestations of systemic autoimmunity. If this result is the effect of a particular antibody, then this antibody may have the capacity to influence the maturation of the immune response toward alleviating the disease in other species. For example, such an antibody could be isolated by biochemical methods, by recombinant DNA methods or by hybridoma monoclonal methods, humanized using standard technology and then administered to patients as a specific therapeutic agent for disease. T cell receptors or cytokines could be equally useful.

Assays.

Subsets of antigenic peptides have the potential to identify patients at risk for particular clinical manifestations or patients in particular prognostic groups. The peptides disclosed herein can be used in combination in assays, such as the solid phase assay, to classify patients.

Specifically, the peptides that are bound by autoantibodies in patients characterized by specific disorders, such as renal disease or central nervous system involvement, are selected and combined in an assay, such as an ELISA for a test to detect the collection autoantibodies that bind this particular collection of peptides. Using a mixture of peptides may increase the efficiency and reliability of such assays, as compared with using a single autoantigen, or a single peptide.

The peptides can be used in solution or immobilized to a solid substrate, such as a gel suitable for affinity chromatography, or a multi-well plate, using standard techniques such as the commercially available cyanogen bromide.

The peptides can be used therapeutically in combination with a pharmaceutically acceptable carrier. The peptides can be administered in a dosage effective to block autoantibodies or as a vaccine to block the autoantibodies, by eliciting an immune response. The peptide acts as a functional antagonist by binding to antibody that does not stimulate or activate the immune cells and thereby block the immune response to the autoantigens.

Pharmaceutical carriers are known to those skilled in the art and include encapsulation of compounds for oral administration, for example, in an enteric coating or in combination with a binder such as stearate or lactose, or in solution. Acceptable solutions include sterile water, saline, and buffered solutions at physiological pH. Peptides used as vaccines can be administered orally, intramuscularly or subcutaneously. Other compounds will be administered according to standard procedures used by those skilled in the art. As defined herein, a pharmaceutical carrier is usually inert by itself but may have biological activity. For example, a vaccine may consist of immunogenic peptides or proteins in combination with an adjuvant.

Alternatively, the peptides used for treatment might include peptides homologous to an identified antigenic sequence. These peptides, either free or bound to a carrier, could be delivered to a patient in order to decrease the amount of circulating antibody with a particular specificity. In addition, knowledge of the cross-reacting epitopes between a foreign antigen and an autoantigen may allow for re-induction of tolerance. It is well known in experimental models of the immune response that the response can be suppressed and tolerance induced by treatment with the antigen. Peptide therapy with the cross-reacting sequences may be a potential therapy in autoimmune diseases.

The amino acid sequences can also be used to make agents for neutralizing circulating antibodies or immobilized on substrates in extracorporeal devices for specific removal of autoantibodies, using methodology known to those skilled in the art.

The one letter amino acid code used in the figures and following examples is presented below:

| | | |
|---|---|---|
| A - alanine | I - isoleucine | R - arginine |
| C - cysteine | K - lysine | S - serine |
| D - aspartic acid | L - leucine | T - threonine |
| E - glutamic acid | M - methionine | V - valine |
| F - phenylalanine | N - asparagine | W - tryptophan |
| G - glycine | P - proline | Y - tyrosine |
| H - histidine | Q - glutamine | |

The present invention will be further understood with reference to the following non-limiting examples:

EXAMPLE 1

Identification of Linear Epitopes of the 60 kD Ro/SSA Protein

Peptides that represent linear epitopes for the 60 kD protein are shown in Table 1. These data represent the average result from seven normal sera, twelve SLE sera of which eight were strong anti-Ro/SSA precipitin positive sera, and the anti-Ro/SSA affinity purified autoantibody from the same four anti-Ro/SSA precipitin positive patient sera. The data has been multiplied by a constant in each case so that the magnitude of the binding could be compared at a constant IgG concentration, loo micrograms IgG per milliliter in these results.

This study demonstrates that the anti-Ro/SSA peptide binding activity is enriched in parallel with the anti-Ro/SSA activity directed against the native molecule. The specific binding activity against both the antigenic peptides and the Ro/SSA antigen increased by about three-fold by the affinity enrichment procedure, indicating that peptide binding is part of the overall anti-Ro/SSA response.

The first and second columns of Table 1 identify the sequences bound above a threshold of $A_{410}$ of 0.3. This threshold was chosen because none of the peptides were bound by the normal sera by an average of greater than $A_{410}=0.3$. The first column in Table 1 identifies the amino acid residues of the first amino acid of each octapeptide. This is also called the octapeptide number. The second column presents the amino acid sequences. Note that this information is presented in two ways. First, the inclusive octapeptide numbers along with the respective inclusive amino acid sequences are presented. Second, each antigenic octapeptide is individually identified along with its sequence.

TABLE 1

Average binding of anti-RO/SSA sera to octapeptides constructed from the sequence of the 60 Kd RO/SSA peptide greater than $A_{410}$ of 0.3.

| Anti-Ro/SSA Sera (Octapeptide Number) | Sequence | |
|---|---|---|
| 45–48 | TYYIKEQKLGL | (Sequence ID NO.6) |
| 45 | TYYIKEQK | (Sequence ID NO.7) |
| 46 | YYIKEQKL | (Sequence ID NO.8) |
| 47 | YIKEQKLG | (Sequence ID NO.9) |
| 48 | IKEQKLGL | (Sequence ID NO.10) |
| 81–82 | SQEGRTTKQ | (Sequence ID NO.11) |
| 81 | SQEGRTTK | (Sequence ID NO.12) |
| 82 | QEGRTTKQ | (Sequence ID NO.13) |
| 106–108 | STKQAAFKAV | (Sequence ID NO.14) |
| 106 | STKQAAFK | (Sequence ID NO.15) |
| 107 | TKQAAFKA | (Sequence ID NO.16) |
| 108 | KQAAFKAV | (Sequence ID NO.17) |
| 126–133 | FTFIQFKKDLKESMK | (Sequence ID NO.18) |
| 126 | FTFIQFKK | (Sequence ID NO.19) |
| 127 | TFIQFKKD | (Sequence ID NO.20) |
| 128 | FIQFKKDL | (Sequence ID NO.21) |
| 129 | IQFKKDLK | (Sequence ID NO.22) |
| 130 | QFKKDLKE | (Sequence ID NO.23) |
| 131 | FKKDLKES | (Sequence ID NO.24) |
| 132 | KKDLKESM | (Sequence ID NO.25) |
| 133 | KDLKESMK | (Sequence ID NO.26) |
| 139–140 | MKCGMWGRA | (Sequence ID NO.27) |
| 139 | MKCGMWGR | (Sequence ID NO.28) |
| 140 | KCGMWGRA | (Sequence ID NO.29) |
| 143–146 | MWGRALRKAIA | (Sequence ID NO.30) |

TABLE 1-continued

Average binding of anti-RO/SSA sera to octapeptides constructed from the sequence of the 60 Kd RO/SSA peptide greater than $A_{410}$ of 0.3.

| Anti-Ro/SSA Sera (Octapeptide Number) | Sequence | |
|---|---|---|
| 143 | MWGRALRK | (Sequence ID NO.31) |
| 144 | WGRALRKA | (Sequence ID NO.32) |
| 145 | GRALRKAI | (Sequence ID NO.33) |
| 146 | RALRKAIA | (Sequence ID NO.34) |
| 165–173 | ALAVTKYKQRNGWSHK | (Sequence ID NO.35) |
| 165 | ALAVTKYK | (Sequence ID NO.36) |
| 166 | LAVTKYKQ | (Sequence ID NO.37) |
| 167 | AVTKYKQR | (Sequence ID NO.38) |
| 168 | VTKYKQRN | (Sequence ID NO.39) |
| 169 | TKYKQRNG | (Sequence ID NO.40) |
| 170 | KYKQRNGW | (Sequence ID NO.41) |
| 171 | YKQRNGWS | (Sequence ID NO.42) |
| 172 | KQRNGWSH | (Sequence ID NO.43) |
| 173 | QRNGWSHK | (Sequence ID NO.44) |
| 183–184 | LRLSHLKPS | (Sequence ID NO.45) |
| 183 | LRLSHLKP | (Sequence ID NO.46) |
| 184 | RLSHLKPS | (Sequence ID NO.47) |
| 198–203 | VTKYITKGWKEVH | (Sequence ID NO.48) |
| 198 | VTKYITKG | (Sequence ID NO.49) |
| 199 | TKYITKGW | (Sequence ID NO.50) |
| 200 | KYITKGWK | (Sequence ID NO.51) |
| 201 | YITKGWKE | (Sequence ID NO.52) |
| 202 | ITKGWKEV | (Sequence ID NO.53) |
| 203 | TKGWKEVH | (Sequence ID NO.54) |
| 212 | LYKEKALS | (Sequence ID NO.55) |
| 222 | TEKLLKYL | (Sequence ID NO.56) |
| 231–234 | AVEKVKRTKDE | (Sequence ID NO.57) |
| 231 | AVEKVKRT | (Sequence ID NO.58) |
| 232 | VEKVKRTK | (Sequence ID NO.59) |
| 233 | EKVKRTKD | (Sequence ID NO.60) |
| 234 | KVKRTKDE | (Sequence ID NO.61) |
| 257–266 | HLLTNHLKSKEVWKALL | (Sequence ID NO.62) |
| 257 | HLLTNHLK | (Sequence ID NO.63) |
| 258 | LLTNHLKS | (Sequence ID NO.64) |
| 259 | LTNHLKSK | (Sequence ID NO.65) |
| 260 | TNHLKSKE | (Sequence ID NO.66) |
| 261 | NHLKSKEV | (Sequence ID NO.67) |
| 262 | HLKSKEVW | (Sequence ID NO.68) |
| 263 | LKSKEVWK | (Sequence ID NO.69) |
| 264 | KSKEVWKA | (Sequence ID NO.70) |
| 265 | SKEVWKAL | (Sequence ID NO.71) |
| 266 | KEVWKALL | (Sequence ID NO.72) |
| 280–283 | ALLRNLGKMTA | (Sequence ID NO.73) |
| 280 | ALLRNLGK | (Sequence ID NO.74) |
| 281 | LLRNLGKM | (Sequence ID NO.75) |
| 282 | LRNLGKMT | (Sequence ID NO.76) |
| 283 | RNLGKMTA | (Sequence ID NO.77) |
| 308–316 | LCNEKLLKKARIHPFH | (Sequence ID NO.78) |
| 308 | LCNEKLLK | (Sequence ID NO.79) |
| 309 | CNEKLLKK | (Sequence ID NO.80) |
| 310 | NEKLLKKA | (Sequence ID NO.81) |
| 311 | EKLLKKAR | (Sequence ID NO.82) |
| 312 | KLLKKARI | (Sequence ID NO.83) |
| 313 | LLKKARIH | (Sequence ID NO.84) |
| 314 | LKKARIHP | (Sequence ID NO.85) |
| 315 | KKARIHPF | (Sequence ID NO.86) |
| 316 | KARIHPFH | (Sequence ID NO.87) |
| 330–339 | TYKTGHGLRGKWRPD | (Sequence ID NO.88) |
| 330 | TYKTGHGL | (Sequence ID NO.89) |
| 331 | YKTGHGLR | (Sequence ID NO.90) |
| 332 | KTGHGLRG | (Sequence ID NO.91) |
| 333 | TGHGLRGK | (Sequence ID NO.92) |
| 334 | GHGLRGKL | (Sequence ID NO.93) |
| 335 | HGLRGKLK | (Sequence ID NO.94) |
| 336 | GLRGKLKW | (Sequence ID NO.95) |
| 337 | LRGKLKWR | (Sequence ID NO.96) |
| 338 | RGKLKWRP | (Sequence ID NO.97) |
| 339 | GKLKWRPD | (Sequence ID NO.98) |
| 355–357 | AAFYKTFKTV | (Sequence ID NO.99) |
| 355 | AAFYKTFK | (Sequence ID NO.100) |

TABLE 1-continued

Average binding of anti-RO/SSA sera to octapeptides constructed from the sequence of the 60 Kd RO/SSA peptide greater than $A_{410}$ of 0.3.

| Anti-Ro/SSA Sera (Octapeptide Number) | Sequence | |
|---|---|---|
| 356 | AFYKTFKT | (Sequence ID NO.101) |
| 357 | FYKTFKTV | (Sequence ID NO.102) |
| 362–366 | KTVEPTGKRFLL | (Sequence ID NO.103) |
| 362 | KTVEPTGK | (Sequence ID NO.104) |
| 363 | TVEPTGKR | (Sequence ID NO.105) |
| 364 | VEPTGKRF | (Sequence ID NO.106) |
| 365 | EPTGKRFL | (Sequence ID NO.107) |
| 366 | PTGKRFLL | (Sequence ID NO.108) |
| 449–453 | LPMIWAQKTNTP | (Sequence ID NO.109) |
| 449 | LPMIWAQK | (Sequence ID NO.110) |
| 450 | PMIWAQKT | (Sequence ID NO.111) |
| 451 | MIWAQKTN | (Sequence ID NO.112) |
| 452 | IWAQKTNT | (Sequence ID NO.113) |
| 453 | WAQKTNTP | (Sequence ID NO.114) |
| 482–489 | ALREYRKKMDIPAKL | (Sequence ID NO.115) |
| 482 | ALREYRKK | (Sequence ID NO.116) |
| 483 | LREYRKKM | (Sequence ID NO.117) |
| 484 | REYRKKMD | (Sequence ID NO.118) |
| 485 | EYRKKMDI | (Sequence ID NO.119) |
| 486 | YRKKMDIP | (Sequence ID NO.120) |
| 487 | RKKMDIPA | (Sequence ID NO.121) |
| 488 | KKMDIPAK | (Sequence ID NO.122) |
| 489 | KMDIPAKL | (Sequence ID NO.123) |

EXAMPLE 2

Characterization of Initial Human anti-Spliceosomal Autoimmune Response and Expansion Pattern Over Time with Systemic Lupus Erythematosus Sera Elucidation of the agent(s) that induce(s) autoimmunity can be used to develop early diagnostic methods for detection of these disorders before irreversible organ damage occurs and additional therapeutics for the prevention and treatment of these disorders. The first method is specifically applied to determine the etiologic or antigenic or immunogenic agent which elicits an autoimmune response in systemic lupus erythematosus patients with anti-spliceosomal or anti-Ro autoimmunity.

The methodology which can be applied to determine the antigenic or etiologic agent for any autoimmune disorder, potentially autoimmune disease, or disease with immune manifestations, was specifically applied to the determination of a peptide which elicits anti-spliceosomal autoimmunity or anti-Ro autoimmunity in both human responses and in peptide-induced animal models of systemic lupus erythematosus.

Synthesis of Overlapping Octapeptides of the Sm B/B', Sm D, nRNP 70K, nRNP A, nRNP C, and 60 kD Ro Autoantigens The published sequence of Sm B/B', Sm D, nRNP 70K, nRNP A, nRNP C, and 60 kD Ro (van Dam, et al. *EMBO J.* 8:3853–3860, 1989; Schmauss, et al. *Nucleic Acids Res.* 17:1733–1743, 1989; Rokeach, et al. *J. Biol. Chem.* 264:5024–30, 1989; Sharpe, et al. *FEBS Lett.* 250:585–590, 1989; Ohosone, et al. *Proc. Natl. Acad. Sci. USA* 86:4249–4253, 1989; Rokeach, et al. *Proc. Natl. Acad. Sci. USA* 85:4832–36, 1988; Query, et al. *Cell* 57:89–101, 1989; Spritz, et al. *Nucleic Acid Res.* 15: 10373–91, 1987; Theissen, et al. *EMBO J.* 5:3209–17, 1986; Sillekens, et al. *EMBO J.* 6:3841-48, 1987; Sillekens, et al. 16:8307-21, 1988; Deutscher et al. *Proc. Natl. Acad. Sci. USA* 85:9457-83, 1988; Ben-Chetrit, et al. *J. Clin. Invest.* 83:1284-92, 1989) was used to construct all the possible overlapping octapeptides of each individual peptide. A total of over 7000 octapeptides have been constructed from these sequences, with duplicates being synthesized for quality assurance. The amino acids used for peptide synthesis have had Fmoc protected primary amino groups and t-butyl or other appropriate group protected side chains.

Overlapping octapeptides were simultaneously synthesized at the rounded ends of radiation derivatized polyethylene pins which were arranged in the format of a 96 well microtiter plate (Cambridge Research Biochemicals, Cambridge, UK and Coselco Mimotopes Pty Ltd, Victoria, Australia) as described by Geysen, et al. *Proc. Natl. Acad. Sci. USA* 81:3998–4002, 1984; Scofield, R. H. and Harley, J. B. *Proc. Natl. Acad. Sci. USA* 88:3343–3347, 1991. The active esters of Fmoc, t-butyl amino acid solutions (30 mM) were solubilized in N,N-dimethylformamide (DMF) which had 1-hydroxy-benzotriazole added to a final concentration of 30 mM and dispensed into the wells of a microtiter plate. Each amino acid was added as determined by the 240 amino acids of the Raji cell Sm B/B' sequence (van Dam, et al. *EMBO J.* 8:3853–3860, 1989; Schmauss, et al. *Nucleic Acids Res.* 17:1733–1743, 1989; Rokeach, et al. *J. Biol. Chem.* 264:5024–30, 1989). After 18 hours of incubation, the pins were washed in DMF for 5 minutes, four times at two minutes each in methanol and once again in DMF for 5 minutes. The Fmoc protecting groups were then removed from the newly added amino acid by a 20% piperidine/DMF bath for 30 minutes. These steps were repeated until all eight amino acids were added. After the final amino acid was added, the amino terminal groups of each peptide was acetylated by incubating the pins in a 5:2:1 (v/v/v) mixture of DMF:acetic anhydride:triethylamine for 90 minutes at room temperature. After this step, the pins were again washed in DMF for 2 minutes, four times at two minutes each in methanol, and then air-dried for 10 minutes. Finally, side chain amino protecting groups were removed by 95:2.5:2.5 (v/w/v) of trifluoracetic acid:phenol:ethanedithiol. Wash steps again included two minutes in methylene chloride, two times at five minutes each in 5% diisopropylethylene/methylene chloride and a final methylene chloride wash for 5 minutes. After drying for 10 minutes, pins were placed in distilled water for 2 minutes, transferred to a methanol bath for 18 hours and dried under vacuum for 18 hours. Control pins composed of amino acids in a random sequence were prepared which were not present in any of the Sm or nRNP antigen sequences. In addition, positive control pins were synthesized from a known reactive sequence of the La/SSB peptide.

Wash steps and incubations were carried out in sealed plastic containers. Other assay steps were performed by lowering the pins into microtiter plate wells. First, pins were blocked with 3% low-fat milk in phosphate buffered saline (PBS) for one hour at room temperature. Pins were then incubated in 1:100 dilutions of sera in PBS with 0.05% Tween (PBST) and 3% milk overnight at 4° C. in humidified sealed containers. The pin blocks were then washed four times with PBST for 10 minutes each with vigorous agitation. Next, each pin was incubated with anti-human gamma chain specific IgG raised in a goat, affinity purified and conjugated to alkaline phosphatase (Jackson Immunoresearch Laboratories, West Grove, Pa.) at a 1:10,000 dilution. Para-nitrophenyl phosphate disodium was used as a substrate for alkaline phosphatase and plates were read at 405 nm with a MicroElisa™ Reader (Dynatech, Alexandria, Va.) Results for each plate were then standardized by comparison with positive control pins. The same control pins were used for all plates and were allowed to develop to a specific O.D. with a known concentration of a standard control sera.

After completion of an assay, pins were sonicated for two hours in sonication buffer (40 g sodium dodecyl sulfate, 4 ml beta-mercaptoethanol and 62.4 g sodium phosphate to 4 liters) to remove antibodies, conjugate and substrate. After sonication, pins were washed twice in hot water and boiled in methanol for 2 minutes. Pins were then allowed to air dry for a minimum of 10 minutes and were stored with desiccant or used for another assay.

Elucidation of the Major Antigenic Regions of the Sm B/B', Sm D, nRNP 70K, nRNP A and nRNP C Autoantigens The average binding of sera containing antibodies specific for Sm B/B', Sm D, nRNP 70K, nRNP A and nRNP C are presented in FIG. 1. In virtually all of these cases the average of control sera from normals is not different from that of patients who do not have the particular specificity presented. The one exception is binding to the $(GR)_{10}$ (Sequence ID No.126) sequence of Sm D, which appears to be bound by sera from lupus patients, whether or not they have Sm or bind Sm D in immunoblot.

Forty octapeptides bound by sera with anti-Sm and anti-nRNP autoantibodies which appear to be epitopes have been identified. These are shown in Table 2. They are bound by over half of the patients with the respective Sm or nRNP autoantibodies and are bound by more than two standard deviations above controls. The absorption, inhibition and other confirmatory studies performed with representative peptides to this point are consistent with their being epitopes.

Determination of the Major Initial Anti-peptide Response of anti-Sm B/B' Systemic Lupus Erythematosus Patient Sera Patient serum which contains both anti-Sm and anti-nRNP autoantibodies has a very homogeneous pattern of binding to the overlapping octapeptides of Sm B/B'. All patient sera tested bind five identical regions of B/B'. Four of these epitopes are proline-rich, near homologous regions: PPPGMRPP (Sequence ID No.1) (which is repeated three times in the carboxyl region of the protein) and PPPGIRGP (Sequence ID No.2). These anti-peptide responses have proven interesting in several ways.

These proline-rich, carboxyl terminal regions of Sm B/B' are the first targets of the anti-Sm response that were able to be detected in two systemic lupus erythematosus patient sera tested. FIG. 2 presents the expansion of the anti-Sm B/B' response in an anti-Sm and anti-nRNP precipitin positive patient sera over a two-year time interval. The initial response of this patient immune response is to PPPGMRPP (Sequence ID No.1) and PPPGIRGP (Sequence ID No.2). Over time this autoimmune process against Sm B/B' spreads to fifteen regions of the protein.

Second, these peptides have been synthesized in bulk (milligram quantities) on a branching poly-lysine (Map™, Applied Biosystems, Calif.) backbone. Map™ is a pyramid of fifteen lysines upon which eight peptides are added to form a multiple antigenic structure. These reagents have allowed the screening of large numbers of lupus and normal control sera. Only systemic lupus erythematosus patient sera with anti-Sm autoantibodies bind either of these sequences.

Third, these two sequences of Sm B/B' are the targets of two anti-Sm monoclonal antibodies. These murine monoclonals, developed from MRL lpr/lpr mice by David Williams of the Kennedy Institute in London, U.K., KSm 5 and KSm 3, both bind Sm B/B' in immunoblot. KSm 5 binds only the repeated PPPGMRPP (Sequence ID No.1) sequence of B/B', while KSm 3 binds the near homologous, PPP-GIRGP (Sequence ID No.2) and PGIRGPPP (Sequence ID No.124) octapeptides. The binding requirements of these two monoclonals appear to be different based upon amino acid substitution and molecular modelling experiments.

Finally, antibodies directed against these peptides are not only the initial target of anti-Sm antibodies but these peptides also constitute a significant portion of the total anti-Sm response in systemic lupus erythematosus patients. Four patient sera have been absorbed over PPPGMRPP (Sequence ID No.1) and PPPGIRGP (Sequence ID No.2) columns and these anti-peptide antibodies correspond to 35 to 60% of the patient anti-Sm response. These percentages vary based upon the amount of patient serum binding to other regions of the Sm B/B' and D proteins.

The same methodology to determine the initial response to the Sm B/B' proteins in human lupus sera which contain anti-spliceosomal antibodies can also be applied to other autoantigen systems. These experiments would lead to the initial anti-peptide responses in autoantibody systems such as anti-nRNP, anti-Ro, anti-La and anti-pyruvate dehydrogenase E2 autoantigen systems, to identify a few examples.

Elucidation of the Major Antigenic Regions of the 60 kD Ro Autoantigen

The fine specificity of the anti-Ro response with the 531 overlapping octapeptides which span the 60 kD Ro protein shows varying patient sera binding patterns which share approximately sixteen regions of common binding. The quality of data in this system is comparable to that shown in FIG. 2. The studies described below further support the concept that the peptides are bound by specific autoantibodies from the lupus patients with anti-Ro autoantibodies.

Two of the major antigenic regions of 60 kD Ro which are recognized by the greatest majority of anti-Ro systemic lupus erythematosus patient sera tested are two peptides which span amino acids 274 through 292 and span amino acids 480 through 494. These sequences are presented below and have been used in rabbit immunization protocols.

EXAMPLE 3

Rabbit Immunization with Initial Antigenic Peptides or Major Antigenic Peptides Recognized by Human Systemic Lupus Erythematosus Sera and the Subsequent Development of Expanded Lupus Autoimmunity Rabbit Immunization Procedure for PPPGMRPP (Sequence ID No.1) and PPPGIRGP (Sequence ID No.2) Peptides of the Sm B/B' Protein Each of two six pound, male New Zealand white rabbits (Shacktele Brothers, Missouri) were immunized with Map™-PPPGMRPP (Sequence ID No.1) (designated GMR1 and GMR2) or with Map™-PPPGIRGP (Sequence ID No.2) (GIR1 and GIR2) using 0.5 mg of peptide suspended in physiological saline and added to an equal volume of Freund's Complete Adjuvant (total volume 2 ml) injected half intraperitoneally and half in two locations subcutaneously. Additional boosting injections with the same protocol occurred on day 26 and day 43.

After the first and second boosting injections, rabbits were bled by cardiac puncture on weekly intervals. Shortly after the fifth bleed GMR2 and GIR1 had adverse reactions to the anesthesia (ketamine HCl/Rompun) and died. Collections of blood after the fifth bleed were done without anesthesia by ear vein. Surviving rabbits were boosted again as above on day 99 and were finally boosted intravenously with 0.5 mg of peptide in physiological saline on day 152.

Immunological Reactivity of the PPPGMRPP (Sequence ID No.1) and PPPGIRGP (Sequence ID No.2) Immunized Rabbit Sera By the second immunized bleed, each rabbit serum bound the peptide of immunization. In addition, the rabbits immunized with PPPGMRPP (Sequence ID No.1) also initially bound the PPPGIRGP (Sequence ID No.2) sequence of Sm B/B'; however, two additional weeks were required before anti-PPPGMRPP (Sequence ID No.1) antibodies were detected in the sera of PPPGIRGP (Sequence ID No.2) immunized rabbits. Titers to both of these peptides increased immediately after boosting and anti-peptide levels remained relatively constant after the seventh immunized bleed. Antibody binding to these peptides is detectable even at dilutions of one to ten million.

Figure 4:
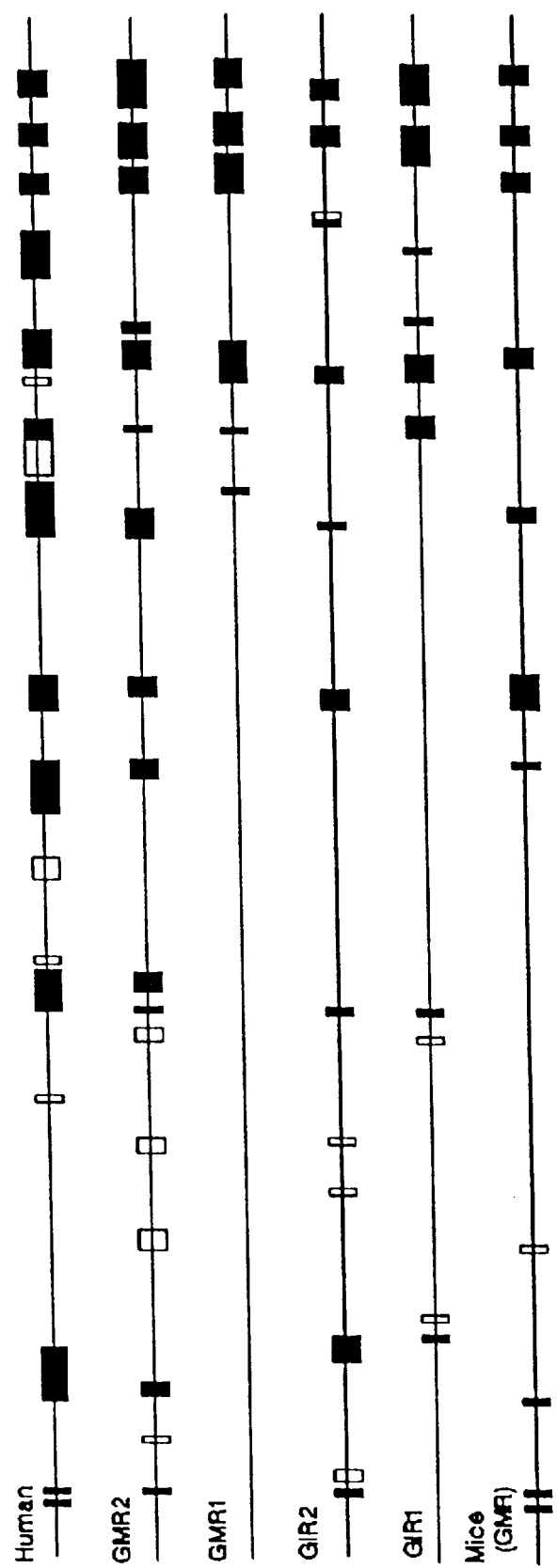
FIG. 4 is a histogram of the antigenic regions of Sm B/B' with human lupus sera, peptide-immunized rabbit sera, and peptide-immunized mouse sera. The average binding of ten Sm, nRNP precipitin positive lupus patients is presented by boxes on the first line. The four individual rabbit sera are presented in the next four lines, with sera being collected ten weeks after immunization for GMR2 and GIR1 and twenty weeks after immunization for GMR1 and GIR2. The reactivity of three pooled PPPGMRPP (Sequence ID No.1) immunized mice bled 42 days after immunization is shown in the last line (GMR). Solid boxes denote shared reactivity between an immunized animal and a naturally occurring human lupus response.
Figure 5A:
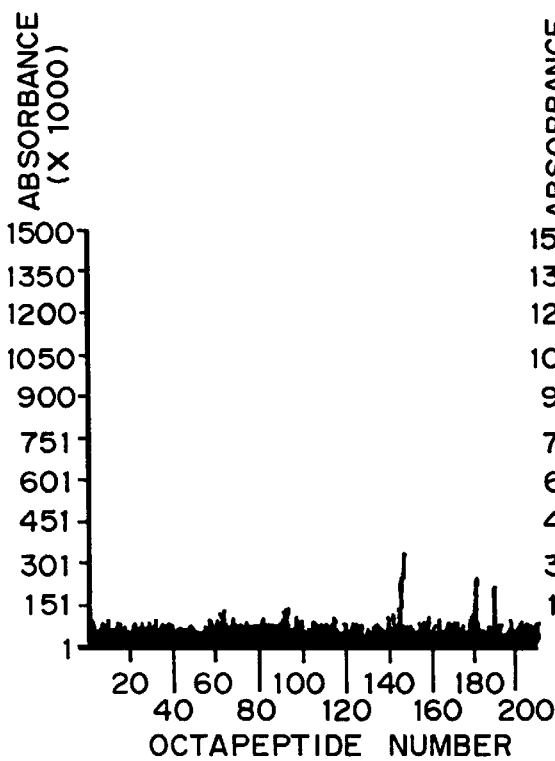
FIGS. 5A, 5B, 5C and 5D present the development of the anti-Sm B/B' response in one PPPGMRPP immunized rabbit. Panel 5A presents the pre-immune serum binding of rabbit GMR2. Panel 5B is serum collected three weeks after immunization. Panels 5C and 5D are assays of sera from collection dates eight and ten weeks after primary immunization.
Figure 5B:
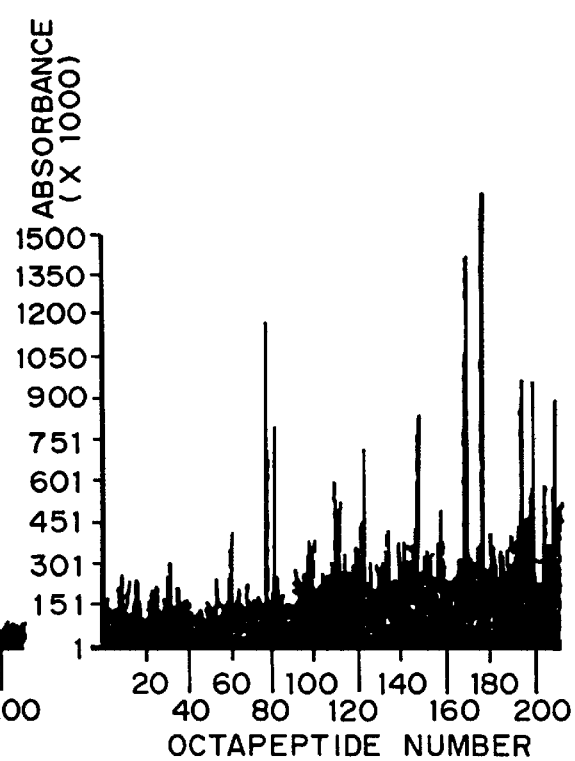
Figure 5C:
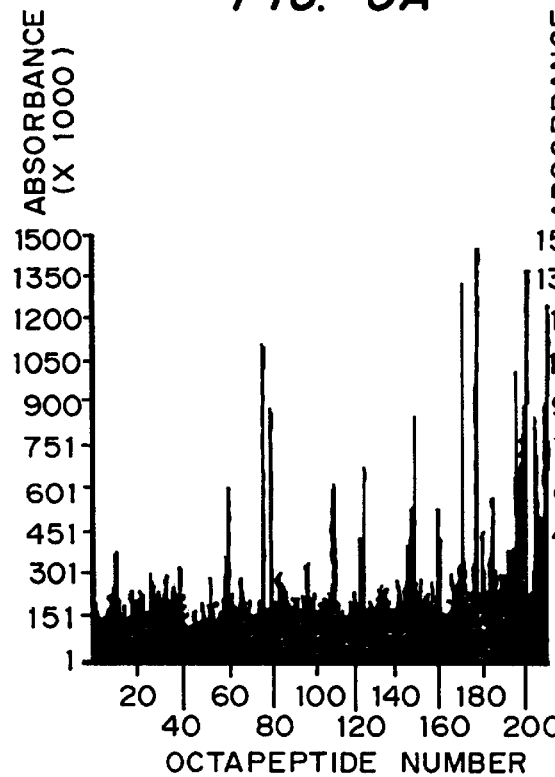
Figure 5D:
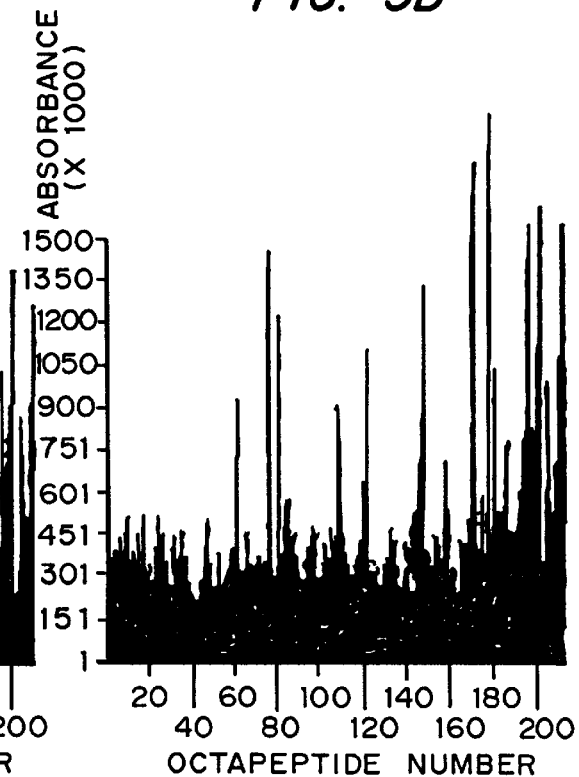

Over time each rabbit has developed antibodies which bind additional regions of Sm B/B' (FIG. 3, Panels B and D; FIG. 4 and FIG. 5). Many of these regions correspond to areas of Sm B/B' which are bound by human systemic lupus erythematosus sera.

As with the spontaneously arising human response, rabbits immunized with peptides (Map™-PPPGMRPP (Sequence ID No.1) or Map-PPPGIRGP (sequence ID No.2)) first bind the proline-rich motifs at the carboxyl terminus (immunization peptides) and spread to several different amino terminal regions of Sm B/B' (FIG. 4).

The critical feature of the model is the spreading of the immune response from simply being directed against the immunization peptide, which, as defined herein, is not necessarily an autoimmune response, to being directed against the autoantigen from which the immunization peptide is derived, which is an autoimmune response.

Additional areas of Sm B/B' are bound by rabbit sera over time (FIG. 5). Data show that binding to the octapeptides numbered 75–76, 79, 122 and 176 found in week three of the immunization protocol represents new antibody specificities. By week four, new binding regions of Sm B/B' at octapeptides 60, 108–110, 145–47 and 168–170 are detected.

These new antibody specificities do not cross react with the original peptide of immunization. Absorption of the immunized rabbit sera over a column composed of only the immunization peptide removes the binding activity with Map™-PPPGMRPP (Sequence ID No.1) and Map™-PPPGIRGP (Sequence ID No.2) sequences. No binding is lost to other regions of Sm B/B'.

These peptide-induced autoimmune responses not only expand to produce antibodies which bind various regions of the protein from which the immunization peptide was selected, these rabbits also produce antibodies which bind to other proteins of the spliceosomal particle. After two months into the immunization protocol, all of the B/B' derived Map™-PPPGMRPP (Sequence ID No.1) and Map™-PPPGIRGP (Sequence ID No.2) immunized rabbits produce antibodies which bind various peptides of Sm D (for an example see Panel A of FIG. 6). These rabbits, after an additional period of time, also produce antibodies which bind to various regions of nRNP 70K, nRNP A and nRNP C (Panels B, C, and D of FIG. 6). Again, these are new antibody specificities, not cross-reactions with the peptide of immunization, because binding of these regions of the nRNP proteins can not be removed by absorption with a column composed of the peptide of immunization.

In addition to a very interesting induced immunoglobulin response toward different regions of the Sm B/B' protein, initial experiments of the reactivity of peripheral blood mononuclear cells from these peptide-immunized rabbits, GMR1 and GIR2, toward peptide and whole antigen are promising. Both GMR1 and GIR2 rabbits have peripheral cells which proliferate in response to both the Map™-PPPGMRPP (Sequence ID No.1) and Map™-PPPGIRGP (Sequence ID No.2) peptides. For example, GMR1 has a stimulation index of 16.2 with Map™-PPPGMRPP (Sequence ID No.1) and of 20.1 with Map™-PPPGIRGP (Sequence ID No.2). These numbers are from the height of an antigen dose response curve and similar results have been obtained in separate experiments. In addition, both of these rabbits have cells which extensively proliferate after incubation with whole Sm and nRNP antigens (stimulation indices above 20). Neither of these rabbits have cells which proliferate in response to peptides derived from the 60 kD Ro antigen, or the entire 60 kD Ro antigen. Control peptides containing the Map™-backbone do not stimulate proliferation.

These results demonstrate that the spreading induced and the patterns of octapeptide binding that result in individual animals closely imitate the spreading and patterns observed in individual human patients, as clearly shown by comparison of the binding pattern of the two patients in FIG. 3 with the two sera from peptide immunized rabbits and the figures of human anti-Sm B/B' development in FIG. 2 and peptide-induced rabbit anti-Sm B/B' development in FIG. 5.

In addition to anti-peptide responses to multiple regions of many, if not all of the Sm and nRNP proteins, these rabbit sera also bind whole Sm and nRNP antigen. All splices some derived peptide immunized rabbit sera bind to Sm and nRNP by ELISA either before or at the fifth immunized bleed. These rabbits can have ELISA titers against nRNP antigen with titers of one to ten-thousand. In addition, these rabbit sera appear to bind the Sm and nRNP antigens in Western blot. The expected molecular weight bands are bound in blots of rabbit thymus extract and human HeLa cell extract. These sera also immunoprecipitate the U RNAs from whole cell lysates.

These immunized rabbit sera have such strong anti-Sm and anti-nRNP titers that both the GMR1 and GIR2 rabbits form precipitin lines in immunodiffusion with these antigens. These rabbits not only satisfy the human lupus criterion for classification by having anti-Sm autoantibodies, but they also have positive anti-nuclear antibody titers at dilutions of up to 1:3240 and 1:540.

These animals are important as models for screening of compounds which (1) induce autoimmunity; (2) inhibit induction of autoimmunity; (3) suppress autoimmunity; (4) are useful in diagnosis of autoimmunity; and (5) are useful as therapeutics for the treatment of autoimmune disorders. Examples of reagents useful in diagnosis include Sm or nRNP antigen, and antisera for the development of sandwich solid phase assays. In sandwich assays a specific antibody reagent is allowed to adhere to the solid phase. Then a source of antigen (or autoantigen) is incubated with the solid phase. The antigen (or autoantigen) adheres to the specific antibody on the solid phase. This complex on the solid phase can be used to assay for the presence of autoantibodies in human sera following a standard enzyme-linked immunosorbent assay.

An example of a therapeutic application would be antibodies, T cell receptors or cytokines that reverse the autoimmune or clinical manifestations of disease. By experimental manipulation or spontaneous development animals may reverse disease-related autoimmunity. Any such improvement would directly lead to potentially important therapeutics. The antibodies, T cell receptors and cytokines in these animals could be tested in other animals. Those that were therapeutically useful could be tested in human and veterinary applications.

EXAMPLE 4

Immunization of Rabbits with Peptide CAIALRBYRKKMDIPA (Sequence ID No.3) from Human 60 kD Ro Additional experiments which parallel those done in the Sm B/B' system described above involve rabbit immunization with antigenic and non-antigenic regions of 60 kD Ro.

Immunization of Rabbits with the Peptide CAIALREYRKKMDIPA (Sequence ID No.3), Derived from Human 60 kD Ro Three rabbits have been immunized with a peptide, CAIALREYRKKMDIPA, that spans amino acids 480–494 of 60 kD Ro and which contains an amino terminal cysteine. This peptide was not built on a Map backbone. Peptides from this region of the 60 kD Ro bound 75% of the precipitin positive anti-Ro patient sera tested.

Figure 7A:
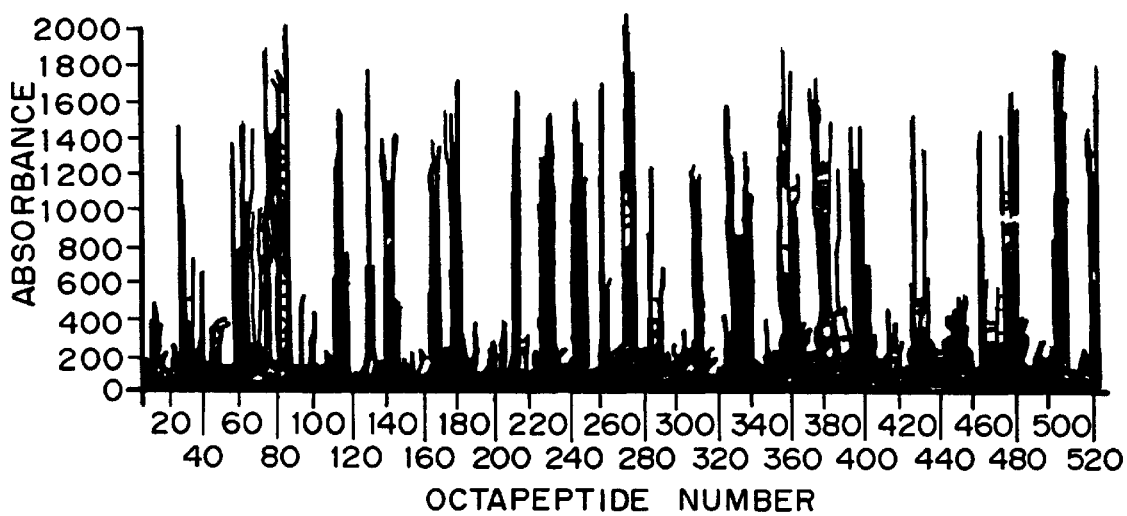
FIGS. 7A and 7B present a comparison of the 60 kD Ro binding regions of a human lupus patient serum and a Ro peptide-immunized rabbit serum. Panel A shows the antigenic regions of a rabbit immunized with Ro 480 (CAIALEYRKKMDIPA) (Sequence ID No.5) twenty weeks after immunization. Panel 7B displays the binding regions of a human lupus patient with precipitating antibodies to Ro.
Figure 7B:
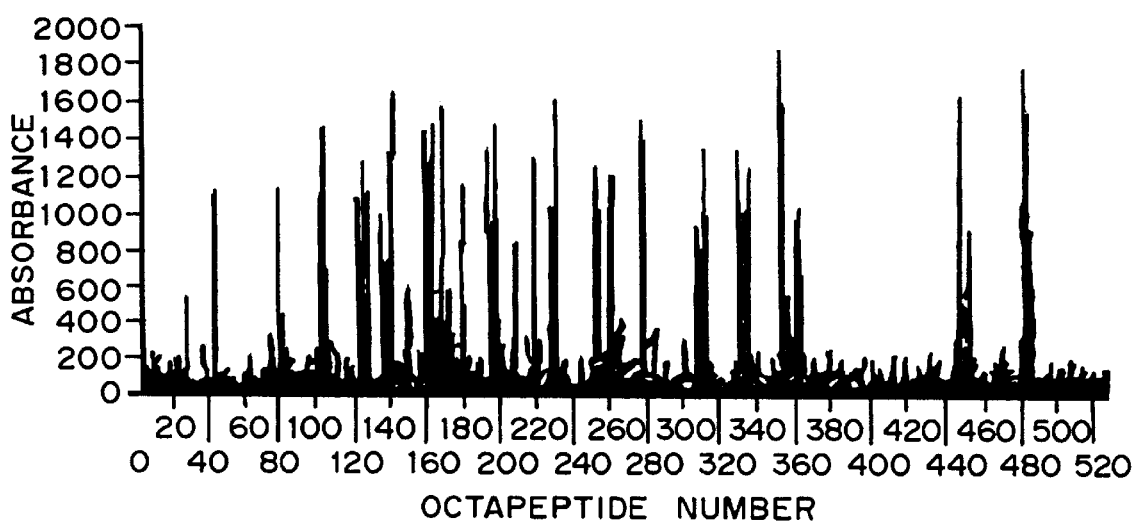
Figure 8A:
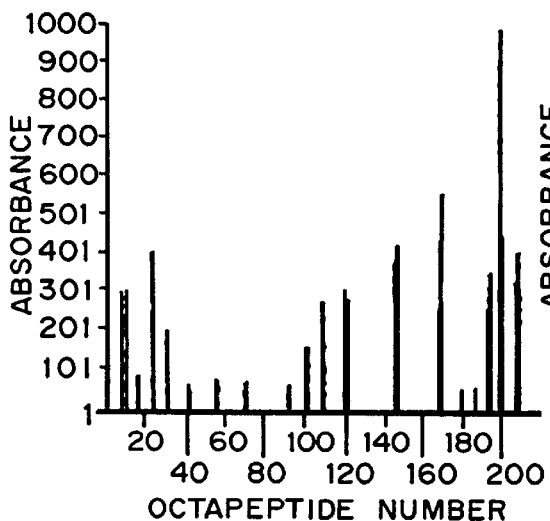
FIGS. 8A, 8B, 8C, and 8D are a comparison of the antigenic regions of one PPPGMRPP (Sequence ID No.1) immunized mouse to one mouse immunized with only Freund's Adjuvant alone as assayed for binding to the Sm B/B' and Sm D overlapping octapeptides. Panel 8A presents the binding of PPPGMRPP (Sequence ID No.1) immunized mouse 19 with specific regions of Sm B/B'. Some regions of reactivity have been determined which are also antigenic regions in human lupus sera; however, all of the overlapping octapeptides were not tested due to the limited amount of mouse serum available. Additional regions of peptide-immunized mouse serum binding to the octapeptide from the Sm D protein are shown in Panel 8C. Control mouse immunized only with Freund's adjuvant serum binding is presented with Sm B/B' octapeptides in Panel 8B and Sm D peptides in Panel 8D.
Figure 8B:
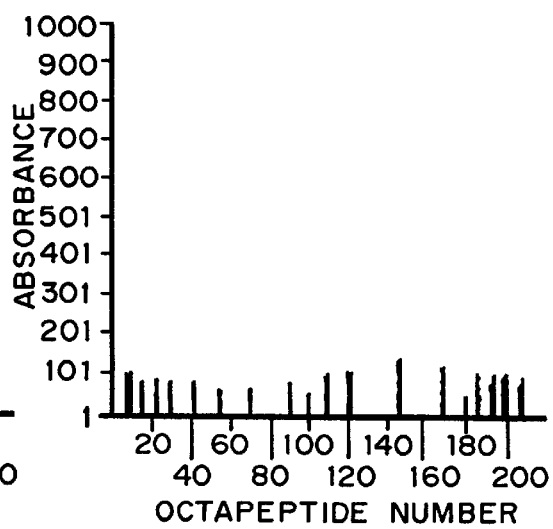
Figure 8C:
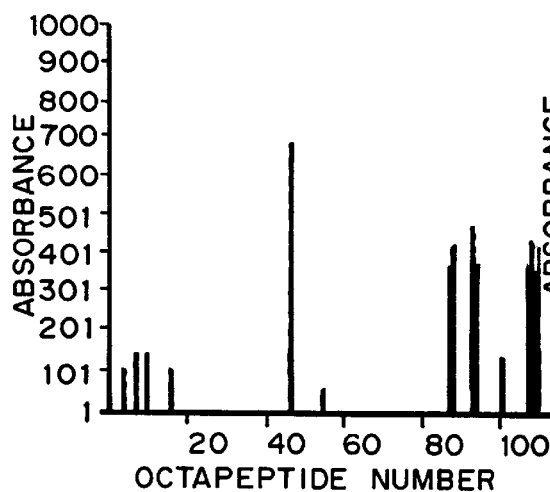
Figure 8D:
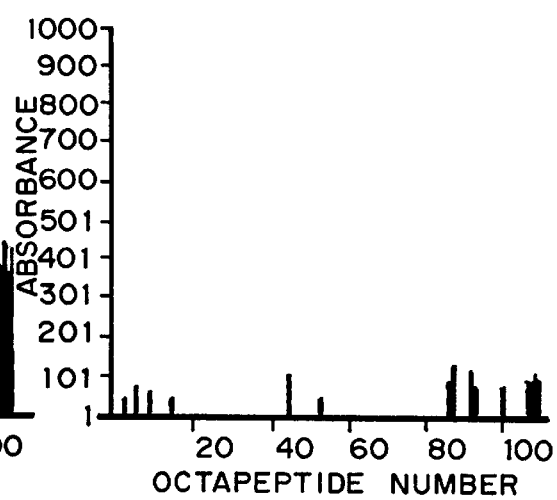

Rabbits immunized with this CAIALREYRKKMDIPA (Sequence ID No.3) peptide bind to many different regions of the 60 kD Ro sequence, in many of the same areas as do anti-Ro patient sera (FIG. 7). These rabbits also bind the regions of Ro which do cross-react as well as octapeptides from regions which do not cross-react with affinity purified patient anti-CAIALREYRKKMDIPA (Sequence ID No.3) (epitopes found at octapeptides 60 and 360). Up to twelve other groups of 60 kD Ro octapeptides bound by these immunized rabbit sera are not removed by absorption with CAIALREYRKKMDIPA (Sequence ID No.3). For the antibodies binding these additional regions of 60 kD Ro there is no evidence for cross-reactivity.

Antibodies in these rabbit sera bind whole Ro antigen as detected by ELISA, Western blot and immunodiffusion analysis. The three rabbits immunized with this peptide have shared regions of antibody binding; however, all three of these rabbits do not expand their response equally to the protein. For example, one rabbit only binds one region of 60 kD Ro, while the other two rabbits bind six and twelve to fifteen groups of octapeptides from Ro, respectively.

Immunization of Rabbits with the Peptide QEMPLTALLRNLGKNTC (Sequence ID No.4), Derived from Human 60 kD Ro Two rabbits have also been immunized with a peptide Ro-274 (amino acids 274–292, QEMPLTALLRNLGKMTC (Sequence ID No.4)) which is also an antigenic region in over 85% of the anti-Ro patient sera tested. The Ro 274 peptide immunized rabbits also bind to several different regions of the 60 kD Ro protein. As with the Map™-PPPGMRPP (Sequence ID No.1) and Map™-PPPGIRGP (Sequence ID No.2) immunized rabbits in the spliceosomal autoantigen system, the binding of other peptides of the protein from which the immunization peptide is obtained expands over time. Also as with the induced spliceosomal response, the initial binding of rabbit antibodies is directed against the peptide of immunization with other peptides being bound by rabbit antibodies over time. These rabbit sera also bind whole bovine Ro antigen as detected by ELISA and Western blot analysis. Spreading to additional regions of Ro occurs much earlier than has been observed in the rabbits immunized with peptides from Sm B/B'.

Immunization of Rabbits with the Peptide, VAPSDEMVPCPVTTDMC (Sequence ID No.25), from 60 kD Ro which is not Autoantigenic in Human anti-Ro Sera Rabbits immunized with the non-antigenic, Ro-413 peptide, VAFSDEMVPCPVTTDMC, mount a different type of immune response against the 60 kD Ro autoantigen. These rabbits produce antibodies which currently bind only the antigenic region of 60 kD Ro with which they were immunized, amino acids 413 through 429. No other antigenic peptide binding of the 60 kD Ro protein has yet been detected and expansion of this immune response to other regions of Ro or La has only been appreciated to regions of the 60 kD Ro protein which are non-antigenic in human systemic lupus erythematosus and human Sjogren's syndrome sera.

In summary, Rabbits immunized with antigenic peptides of 60 kD Ro, CAIALREYRKKMDIPA (Sequence ID No.3) and QEMPLTALLRNLGKMTC (Sequence ID No.4), produce immune responses which expand in a way which parallels those seen in the PPPGMRPP (Sequence ID No.1) and the PPPGIRGP (Sequence ID No.2) immunized rabbits. Rabbits immunized with the non-antigenic Ro 413 peptide produce a different, limited response. In contrast to the immunization with the B/B' peptides described above, the Ro peptides used are free peptide, not bound to a branching lysine backbone, and a different immunization procedure is used, popliteal node injection with subcutaneous boosting. These features of the Ro peptide induced autoimmunity support the generality of the model of peptide induced spliceosomal autoimmunity.

EXAMPLE 5

Development of Systemic Lupus Erythematosus Clinical Manifestations in Immunized Rabbits Having established an anti-Sm autoimmune response in the animals described in examples 1 and 2, the animals were evaluated for other features of human lupus. Rabbit #462, immunized with PPPGMRPP (Sequence ID No.126), rapidly developed anti-spliceosomal antibodies which were subsequently detected by a sensitive solid phase assay, followed by anti-Sm precipitins. Antinuclear antibodies and anti-double stranded DNA antibodies, typical for lupus, developed in parallel. This animal developed proteinuria and had cells and casts in its urine, including pigmented granular casts and red cell casts. Mild renal insufficiency was present with a creatinine as high as 1.7 mg/dl. The proteinuria was measured to be 168 mg/kg/d, which is approximately the level found in a human lupus patient with 8 grams proteinuria per day. The platelet count dropped as low as 27,000 per mcl. This animal is losing hair much more rapidly than controls and has lost 22 ounces, or 18%, of its weight. Rabbit #462 clearly satisfies the criteria for systemic lupus erythematosus (Tan, et al., *Arthritis Rheum.* 25:1271–77, 1982).

Three other rabbits were immunized with PPPGMRPP (Sequence ID No.1) or PPPGIRGP (Sequence ID No.2). Each of these animals developed anti-spliceosomal autoimmunity as measured by antibody binding to the 1201 spliceosomal octapeptides and to purified spliceosome in solid phase assays. Two of these animals died early in the immunization protocol. One died of bowel obstruction unrelated to lupus. The other immunized with PPPGMRPP (Sequence ID No.1) died before being evaluated for lupus. This animal had seizures, a positive antinuclear antibody (1:360) and the most complex anti-spliceosome response at that point in the immunization protocol, as measured by the 18 groups of spliceosome octapeptides bound.

Rabbit #465, immunized with PPPGIRGP, is a long term survivor. This animal has anti-Sm precipitins, a positive antinuclear antibody (1:360), 3+ proteinuria and seizures, all of which are consistent lupus symptoms (Tan, et al.,*Arthritis Rheum.* 25: 1271–77, 1982).

EXAMPLE 6

Mouse Immunization with Initial Antigenic Peptides or Major Antigenic Peptides Recognized by Human Systemic Lupus Erythematosus Sera and the Subsequent Development of Expanded Lupus Autoimmunity.

Experiments with BALB/c mice have shown a very similar peptide-induced production of spliceosomal autoimmunity to that found with the outbred New Zealand rabbits. The initial response to the peptide of immunization is followed by a delayed production of mouse antibody which binds other regions of the Sm B/B' and Sm D proteins.

Mouse Immunization Procedure for Map™-PPPGMRPP (Sequence ID No.1) and Map™-PPPGIRGP (Sequence ID No.2) Peptides of the Sm B/B' Protein Mice were divided into three groups: (1) five six week old male BALB/c mice were immunized with 100 micrograms of Map™-PPPGMRPP (Sequence ID No.1) peptide in Freund's Complete Adjuvant, (2) five BALB/c mice were immunized with 100 micrograms of Map™-PPPGIRGP (Sequence ID No.2) peptide in Freund's Complete Adjuvant, and (3) two additional mice were immunized with saline and Freund's Complete Adjuvant. Boosting injections of the same amount of respective peptide in Freund's Incomplete Adjuvant were made at days 7, 14 and 28. Tail bleeds of each mouse were collected on days 0, 21, 35 and 42. Additional serial samples were collected on a weekly basis.

Sera from Mice Immunized with Map™-PPPGMRPP and Map™-PPPGIRGP

Mouse serum binding to both the peptide of immunization and the highly homologous proline-rich peptide (PPPGMRPP (Sequence ID No.1) and PPPGIRGP (Sequence ID No.2)) has been detected on tail bleeds from days 21, 35 and 42. There is an increasing titer over time. Neither mice immunized with Freund's Complete Adjuvant alone (no peptide) nor the pre-immune sera from any of the immunized mice have any measurable reactivity with the PPPGMRPP (Sequence ID No.1) or PPPGIRGP (Sequence ID No.2) peptides.

The reactivity of mouse sera with the overlapping octapeptides which span the Sm B/B' and Sm D polypeptides was tested. On the day 21 bleed only the proline rich PPPGMRPP (Sequence ID No.1) and PPPGIRGP (Sequence ID No.2) regions were bound by mouse sera from mice which had been immunized with Map™-PPPGMRPP (Sequence ID No.1). By the day 35 bleed, however, mouse serum binding had spread to four additional regions of Sm B/B'. As presented in FIG. 8, even more areas of Sm B/B' and new expansion to Sm D peptides can be appreciated. All of the regions bound by mouse sera are also bound by the peptide-immunized rabbit sera and ten of these eleven regions are also major targets of the human systemic lupus erythematosus anti-Sm response (FIG. 4). Regions of antibody binding that are shared between man, rabbits and mice are presented in FIG. 4 as filled histograms, while the antigenic regions that are not shared are represented as opened histograms.

Mouse Immunization Procedure with Peptides, CAIALREYRKKMDIPA (Sequence ID No.3), QEMPLTALLRNLGKXTC (Sequence ID No.4), and VAPSDEMVPCPVTTDMC (Sequence ID No.125), Derived from Human 60 kD Ro Mice were divided into three groups: (1) five 6 week old male BALB/c mice were immunized with 100 micrograms of CAIALREYRKKMDIPA (Sequence ID No.3) peptide in Freund's Complete Adjuvant, (2) five BALB/C mice were immunized with 100 micrograms of QEMPLTALLRNLGK-MTC (Sequence ID No.4) peptide in Freund's Complete Adjuvant, and (3) five additional BALB/c mice were immunized with 100 micrograms of VAFSDEMVPCPVTTDMC (Sequence ID No.125) peptide in Freund's Complete Adjuvant, as described above for the Map™-PPPGMRPP (Sequence ID No.1) and Map™-PPPGIRGP (Sequence ID No.2) immunized mice. The peptide sequences are derived from the sequence for Ro/SSA with an additional C at one end. Boosting injections of the same amount of respective peptide in Freund's incomplete adjuvant were made at days 7, 14 and 28. Tail bleeds of each mouse were collected on days 0, 21, 35 and 42. Subsequent serial samples were collected weekly.

Sera from Mice Immunized with Antigenic and Non-antigenic Ro Peptides

Mouse serum binding to the peptide of immunization has been detected in tail bleeds from days 21, 35 and 42. Titer decreases with length from immunization or boosting injection. Neither mice immunized with Freund's Complete Adjuvant alone (no peptide) nor the pre-immune sera from any of the immunized mice has any measurable reactivity with the immunization peptides. Sera from mice immunized with either antigenic peptide of 60 kD Ro also bind whole Ro by ELISA.

Modifications and variations of the method and reagents of the present invention will be obvious to those skilled in the art from the foregoing detailed description. Such modifications and variations are intended to come within the scope of the appended claims.

We claim:

1. A method to generate an animal model of systemic lupus erythematosus comprising
immunizing a non-human mammalian animal with a first non-immunoglobulin peptide comprising at least eight amino acids,
wherein the peptide comprises an epitope immunoreactive with an autoantibody from a patient with systemic lupus erythematosus, the epitope consisting of between four and twenty amino acids, wherein the epitope includes at least one region in an amino acid sequence obtained by
identifying in a self-antigen bound by a population of autoantibodies present at an early stage in a patient with systemic lupus erythematosus those amino acid sequences of the self-antigen containing two or more regions immunoreactive with at least two autoantibodies of different epitope specificity,
wherein the peptide is administered in a dosage effective to induce production of autoantibodies immunoreactive with multiple epitopes different from the epitopes present in the first immunizing peptide, thereby generating an animal model of systemic lupus erythematosus.

2. The method of claim 1 wherein the peptide comprises between eight and forty amino acids of a protein selected from the group consisting of SM B/B' and 60 kD Ro protein.

3. The method of claim 1 wherein the epitopes share sequence identity with at least two regions of a viral protein immunoreactive with autoantibodies present in a patient with systemic lupus erythematosus.

4. The method of claim 1 further comprising administering additional non-immunoglobulin peptides immunoreactive with autoantibodies isolated from or detected in a human patient having systemic lupus erythematosus.

5. The method of claim 1 further comprising isolating the autoantibodies from the animal.

6. The method of claim 1 further comprising isolating T cells immunoreactive with self proteins.

7. A method for screening for therapeutics effective in treating autoimmune disorders comprising administering to an animal a compound to be tested for therapeutic effectiveness, wherein the animal has been immunized with a first non-immunoglobulin peptide comprising at least eight amino acids, wherein the peptide comprises an epitope immunoreactive with an autoantibody from a patient with systemic lupus erythematosus, the epitope comprising between four and twenty amino acids, wherein the epitope includes at least one region in an amino acid sequence obtained by identifying in a self-antigen bound by a population of autoantibodies present at an early stage in a patient with systemic lupus erythematosus those amino acid sequences of the self-antigen containing two or more regions immunoreactive with the autoantibodies, wherein the peptide is administered in a dosage effective to induce production of autoantibodies immunoreactive with multiple epitopes different from the immunizing peptide, and determining if the compound is effective to treat the autoimmune disorder.

8. The method of claim 7 wherein the effectiveness is measured as inhibition of the production of autoantibodies.

9. The method of claim 7 wherein the effectiveness is measured as a decrease in the clinical symptoms of autoimmunity.

10. An isolated peptide between eight and twenty amino acids in length immunoreactive with a Ro/SSA autoantibody, comprising at least eight amino acids in an amino acid sequence selected from the group consisting of TYYIKEQKLGL Sequence ID No 6; TYYIKEQK Sequence ID No. 7; YYIKEQKL Sequence ID No. 8; YIKEQKLG Sequence ID No. 9; IKEQKLGL Sequence ID No. 10; VTKYITKGWKEVH Sequence ID No. 48; VTKYITKG Sequence ID No. 49; TKYITKGW Sequence ID No. 50; KYITKGWK Sequence ID No. 51; YITKGWKE Sequence ID No. 52; ITKGWKEV Sequence ID No. 53; TKGWKEVH Sequence ID No. 54; VEPTGKRFL Sequence ID No. 126; VEPTGKRF Sequence ID No. 106; and EPTGKRFL Sequence ID No. 107.

11. The peptide of claim 10 further comprising a pharmaceutical carrier for administration to a patient, wherein the carrier and concentration of sequences elicit an immune response when administered to a host.

12. The peptide of claim 10 labelled with a compound selected from the group consisting of dyes, fluorescent labels, chemiluminescent labels, enzymes, and radioactive labels.

13. The peptide of claim 10 immobilized onto a substrate.

* * * * *

SEQUENCE LISTING (1) GENERAL INFORMATION:

(iii) NUMBER OF SEQUENCES: 127

(2) INFORMATION FOR SEQ ID NO:1:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 1:

Pro Pro Pro Gly Met Arg Pro Pro
1               5

(2) INFORMATION FOR SEQ ID NO: 2:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 2:

Pro Pro Pro Gly Ile Arg Gly Pro
1               5

(2) INFORMATION FOR SEQ ID NO: 3:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 3:

Cys Ala Ile Ala Leu Arg Glu Tyr Arg Lys Lys Met Asp Ile Pro
1               5                   10                  15
Ala (2) INFORMATION FOR SEQ ID NO: 4:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 4:

```
Gln Glu Met Pro Leu Thr Ala Leu Leu Arg Asn Leu Gly Lys Met
1               5                   10                  15

Thr Cys
```

(2) INFORMATION FOR SEQ ID NO: 5:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 5:

```
Cys Ala Ile Ala Leu Glu Tyr Arg Lys Lys Met Asp Ile Pro Ala
1               5                   10                  15
```

(2) INFORMATION FOR SEQ ID NO: 6:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 6:

```
Thr Tyr Tyr Ile Lys Glu Gln Lys Leu Gly Leu
1               5                   10
```

(2) INFORMATION FOR SEQ ID NO: 7:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO

```
        (iv) ANTI-SENSE: NO (v) FRAGMENT TYPE: N-terminal (xi) SEQUENCE DESCRIPTION: SEQ ID NO: 7:

Thr Tyr Tyr Ile Lys Glu Gln Lys
1               5

(2) INFORMATION FOR SEQ ID NO: 8:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 8:

Tyr Tyr Ile Lys Glu Gln Lys Leu
1               5

(2) INFORMATION FOR SEQ ID NO: 9:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 9:

Tyr Ile Lys Glu Gln Lys Leu Gly
1               5

(2) INFORMATION FOR SEQ ID NO: 10:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 10:

Ile Lys Glu Gln Lys Leu Gly Leu
1               5
```

(2) INFORMATION FOR SEQ ID NO: 11:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 11:

Ser Gln Glu Gly Arg Thr Thr Lys Gln
1               5

(2) INFORMATION FOR SEQ ID NO: 12:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 12:

Ser Gln Glu Gly Arg Thr Thr Lys
1               5

(2) INFORMATION FOR SEQ ID NO: 13:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 13:

Gln Glu Gly Arg Thr Thr Lys Gln
1               5

(2) INFORMATION FOR SEQ ID NO: 14:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 14:

Ser Thr Lys Gln Ala Ala Phe Lys Ala Val
1               5                   10

(2) INFORMATION FOR SEQ ID NO: 15:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 15:

Ser Thr Lys Gln Ala Ala Phe Lys
1               5

(2) INFORMATION FOR SEQ ID NO: 16:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 16:

Thr Lys Gln Ala Ala Phe Lys Ala
1               5

(2) INFORMATION FOR SEQ ID NO: 17:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 17:

Lys Gln Ala Ala Phe Lys Ala Val
1               5

(2) INFORMATION FOR SEQ ID NO: 18:

(i) SEQUENCE CHARACTERISTICS:
        (A) LENGTH: 15 amino acids
        (B) TYPE: amino acid (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 18:

Phe Thr Phe Ile Gln Phe Lys Lys Asp Leu Lys Glu Ser Met Lys
1               5                  10                  15

(2) INFORMATION FOR SEQ ID NO: 19:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 19:

Phe Thr Phe Ile Gln Phe Lys Lys
1               5

(2) INFORMATION FOR SEQ ID NO: 20:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 20:

Thr Phe Ile Gln Phe Lys Lys Asp
1               5

(2) INFORMATION FOR SEQ ID NO: 21:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 21:

Phe Ile Gln Phe Lys Lys Asp Leu
1               5

(2) INFORMATION FOR SEQ ID NO: 22:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 22:

Ile Gln Phe Lys Lys Asp Leu Lys
1               5

(2) INFORMATION FOR SEQ ID NO: 23:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 23:

Gln Phe Lys Lys Asp Leu Lys Glu
1               5

(2) INFORMATION FOR SEQ ID NO: 24:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 24:

Phe Lys Lys Asp Leu Lys Glu Ser
1               5

(2) INFORMATION FOR SEQ ID NO: 25:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 25:

Lys Lys Asp Leu Lys Glu Ser Met
1               5

(2) INFORMATION FOR SEQ ID NO: 26:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 26:

Lys Asp Leu Lys Glu Ser Met Lys
1               5

(2) INFORMATION FOR SEQ ID NO: 27:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 27:

Met Lys Cys Gly Met Trp Gly Arg Ala
1               5

(2) INFORMATION FOR SEQ ID NO: 28:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 28:

Met Lys Cys Gly Met Trp Gly Arg
1               5

```
(2) INFORMATION FOR SEQ ID NO: 29:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 29:

Lys Cys Gly Met Trp Gly Arg Ala
1               5

(2) INFORMATION FOR SEQ ID NO: 30:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 30:

Met Trp Gly Arg Ala Leu Arg Lys Ala Ile Ala
1               5                   10

(2) INFORMATION FOR SEQ ID NO: 31:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 31:

Met Trp Gly Arg Ala Leu Arg Lys
1               5

(2) INFORMATION FOR SEQ ID NO: 32:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO
```

(v) FRAGMENT TYPE: N-terminal (xi) SEQUENCE DESCRIPTION: SEQ ID NO: 32:

Trp Gly Arg Ala Leu Arg Lys Ala
1               5

(2) INFORMATION FOR SEQ ID NO: 33:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 33:

Gly Arg Ala Leu Arg Lys Ala Ile
1               5

(2) INFORMATION FOR SEQ ID NO: 34:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 34:

Arg Ala Leu Arg Lys Ala Ile Ala
1               5

(2) INFORMATION FOR SEQ ID NO: 35:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 35:

Ala Leu Ala Val Thr Lys Tyr Lys Gln Arg Asn Gly Trp Ser His
1               5                   10                  15

Lys (2) INFORMATION FOR SEQ ID NO: 36:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 36:

Ala Leu Ala Val Thr Lys Tyr Lys
1               5

(2) INFORMATION FOR SEQ ID NO: 37:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 37:

Leu Ala Val Thr Lys Tyr Lys Gln
1               5

(2) INFORMATION FOR SEQ ID NO: 38:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 38:

Ala Val Thr Lys Tyr Lys Gln Arg
1               5

(2) INFORMATION FOR SEQ ID NO: 39:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 39:

Val Thr Lys Tyr Lys Gln Arg Asn
1               5

(2) INFORMATION FOR SEQ ID NO: 40:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 40:

Thr Lys Tyr Lys Gln Arg Asn Gly
1               5

(2) INFORMATION FOR SEQ ID NO: 41:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 41:

Lys Tyr Lys Gln Arg Asn Gly Trp
1               5

(2) INFORMATION FOR SEQ ID NO: 42:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 42:

Tyr Lys Gln Arg Asn Gly Trp Ser
1               5

(2) INFORMATION FOR SEQ ID NO: 43:

(i) SEQUENCE CHARACTERISTICS:
         (A) LENGTH: 8 amino acids
         (B) TYPE: amino acid

```
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 43:

Lys Gln Arg Asn Gly Trp Ser His
1               5

(2) INFORMATION FOR SEQ ID NO: 44:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 44:

Gln Arg Asn Gly Trp Ser His Lys
1               5

(2) INFORMATION FOR SEQ ID NO: 45:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 45:

Leu Arg Leu Ser His Leu Lys Pro Ser
1               5

(2) INFORMATION FOR SEQ ID NO: 46:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal
```

```
        (xi) SEQUENCE DESCRIPTION: SEQ ID NO: 46:

Leu Arg Leu Ser His Leu Lys Pro
1               5

(2) INFORMATION FOR SEQ ID NO: 47:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 47:

Arg Leu Ser His Leu Lys Pro Ser
1               5

(2) INFORMATION FOR SEQ ID NO: 48:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 48:

Val Thr Lys Tyr Ile Thr Lys Gly Trp Lys Glu Val His
1               5                   10

(2) INFORMATION FOR SEQ ID NO: 49:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 49:

Val Thr Lys Tyr Ile Thr Lys Gly
1               5

(2) INFORMATION FOR SEQ ID NO: 50:

(i) SEQUENCE CHARACTERISTICS:
         (A) LENGTH: 8 amino acids
         (B) TYPE: amino acid
         (C) STRANDEDNESS: single
         (D) TOPOLOGY: linear
```

```
        (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 50:

Thr Lys Tyr Ile Thr Lys Gly Trp
1               5

(2) INFORMATION FOR SEQ ID NO: 51:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 51:

Lys Tyr Ile Thr Lys Gly Trp Lys
1               5

(2) INFORMATION FOR SEQ ID NO: 52:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 52:

Tyr Ile Thr Lys Gly Trp Lys Glu
1               5

(2) INFORMATION FOR SEQ ID NO: 53:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 53:

Ile Thr Lys Gly Trp Lys Glu Val
1               5
```

(2) INFORMATION FOR SEQ ID NO: 54:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 54:

Thr Lys Gly Trp Lys Glu Val His
1          5

(2) INFORMATION FOR SEQ ID NO: 55:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 55:

Leu Tyr Lys Glu Lys Ala Leu Ser
1          5

(2) INFORMATION FOR SEQ ID NO: 56:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 56:

Thr Glu Lys Leu Leu Lys Tyr Leu
1          5

(2) INFORMATION FOR SEQ ID NO: 57:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 57:

Ala Val Glu Lys Val Lys Arg Thr Lys Asp Glu
1               5                   10

(2) INFORMATION FOR SEQ ID NO: 58:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 58:

Ala Val Glu Lys Val Lys Arg Thr
1               5

(2) INFORMATION FOR SEQ ID NO: 59:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 59:

Val Glu Lys Val Lys Arg Thr Lys
1               5

(2) INFORMATION FOR SEQ ID NO: 60:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 60:

Glu Lys Val Lys Arg Thr Lys Asp
1               5

(2) INFORMATION FOR SEQ ID NO: 61:

(i) SEQUENCE CHARACTERISTICS:
            (A) LENGTH: 8 amino acids
            (B) TYPE: amino acid

```
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 61:

Lys Val Lys Arg Thr Lys Asp Glu
1               5

(2) INFORMATION FOR SEQ ID NO: 62:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 62:

His Leu Leu Thr Asn His Leu Lys Ser Lys Glu Val Trp Lys Ala
1               5                   10                  15

Leu Leu (2) INFORMATION FOR SEQ ID NO: 63:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 63:

His Leu Leu Thr Asn His Leu Lys
1               5

(2) INFORMATION FOR SEQ ID NO: 64:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal
```

(xi) SEQUENCE DESCRIPTION: SEQ ID NO: 64:

Leu Leu Thr Asn His Leu Lys Ser
1               5

(2) INFORMATION FOR SEQ ID NO: 65:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 65:

Leu Thr Asn His Leu Lys Ser Lys
1               5

(2) INFORMATION FOR SEQ ID NO: 66:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 66:

Thr Asn His Leu Lys Ser Lys Glu
1               5

(2) INFORMATION FOR SEQ ID NO: 67:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 67:

Asn His Leu Lys Ser Lys Glu Val
1               5

(2) INFORMATION FOR SEQ ID NO: 68:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 68:

His Leu Lys Ser Lys Glu Val Trp
1               5

(2) INFORMATION FOR SEQ ID NO: 69:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 69:

Leu Lys Ser Lys Glu Val Trp Lys
1               5

(2) INFORMATION FOR SEQ ID NO: 70:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 70:

Lys Ser Lys Glu Val Trp Lys Ala
1               5

(2) INFORMATION FOR SEQ ID NO: 71:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 71:

Ser Lys Glu Val Trp Lys Ala Leu
1               5

(2) INFORMATION FOR SEQ ID NO: 72:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 72:

Lys Glu Val Trp Lys Ala Leu Leu
1               5

(2) INFORMATION FOR SEQ ID NO: 73:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 73:

Ala Leu Leu Arg Asn Leu Gly Lys Met Thr Ala
1               5                   10

(2) INFORMATION FOR SEQ ID NO: 74:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 74:

Ala Leu Leu Arg Asn Leu Gly Lys
1               5

(2) INFORMATION FOR SEQ ID NO: 75:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 75:

Leu Leu Arg Asn Leu Gly Lys Met
1               5

(2) INFORMATION FOR SEQ ID NO: 76:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 76:

Leu Arg Asn Leu Gly Lys Met Thr
1               5

(2) INFORMATION FOR SEQ ID NO: 77:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 77:

Arg Asn Leu Gly Lys Met Thr Ala
1               5

(2) INFORMATION FOR SEQ ID NO: 78:

(i) SEQUENCE CHARACTERISTICS:
           (A) LENGTH: 16 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 78:

Leu Cys Asn Glu Lys Leu Leu Lys Lys Ala Arg Ile His Pro Phe
1               5                  10                  15

His

```
(2) INFORMATION FOR SEQ ID NO: 79:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 79:

Leu Cys Asn Glu Lys Leu Leu Lys
1               5

(2) INFORMATION FOR SEQ ID NO: 80:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 80:

Cys Asn Glu Lys Leu Leu Lys Lys
1               5

(2) INFORMATION FOR SEQ ID NO: 81:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 81:

Asn Glu Lys Leu Leu Lys Lys Ala
1               5

(2) INFORMATION FOR SEQ ID NO: 82:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO
```

(v) FRAGMENT TYPE: N-terminal (xi) SEQUENCE DESCRIPTION: SEQ ID NO: 82:

Glu Lys Leu Leu Lys Lys Ala Arg
1               5

(2) INFORMATION FOR SEQ ID NO: 83:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 83:

Lys Leu Leu Lys Lys Ala Arg Ile
1               5

(2) INFORMATION FOR SEQ ID NO: 84:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 84:

Leu Leu Lys Lys Ala Arg Ile His
1               5

(2) INFORMATION FOR SEQ ID NO: 85:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 85:

Leu Lys Lys Ala Arg Ile His Pro
1               5

(2) INFORMATION FOR SEQ ID NO: 86:

(i) SEQUENCE CHARACTERISTICS:
        (A) LENGTH: 8 amino acids
        (B) TYPE: amino acid (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 86:

Lys Lys Ala Arg Ile His Pro Phe
1               5

(2) INFORMATION FOR SEQ ID NO: 87:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 87:

Lys Ala Arg Ile His Pro Phe His
1               5

(2) INFORMATION FOR SEQ ID NO: 88:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 88:

Thr Tyr Lys Thr Gly His Gly Leu Arg Gly Lys Leu Lys Trp Arg
1               5                   10                  15

Pro Asp (2) INFORMATION FOR SEQ ID NO: 89:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal

```
      (xi) SEQUENCE DESCRIPTION: SEQ ID NO: 89:

Thr Tyr Lys Thr Gly His Gly Leu
1               5

(2) INFORMATION FOR SEQ ID NO: 90:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 90:

Tyr Lys Thr Gly His Gly Leu Arg
1               5

(2) INFORMATION FOR SEQ ID NO: 91:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 91:

Lys Thr Gly His Gly Leu Arg Gly
1               5

(2) INFORMATION FOR SEQ ID NO: 92:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 92:

Thr Gly His Gly Leu Arg Gly Lys
1               5

(2) INFORMATION FOR SEQ ID NO: 93:

(i) SEQUENCE CHARACTERISTICS:
          (A) LENGTH: 8 amino acids
          (B) TYPE: amino acid
          (C) STRANDEDNESS: single
          (D) TOPOLOGY: linear
```

(ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 93:

Gly His Gly Leu Arg Gly Lys Leu
1               5

(2) INFORMATION FOR SEQ ID NO: 94:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 94:

His Gly Leu Arg Gly Lys Leu Lys
1               5

(2) INFORMATION FOR SEQ ID NO: 95:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 95:

Gly Leu Arg Gly Lys Leu Lys Trp
1               5

(2) INFORMATION FOR SEQ ID NO: 96:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 96:

Leu Arg Gly Lys Leu Lys Trp Arg
1               5

```
(2) INFORMATION FOR SEQ ID NO: 97:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 97:

Arg Gly Lys Leu Lys Trp Arg Pro
1               5

(2) INFORMATION FOR SEQ ID NO: 98:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 98:

Gly Lys Leu Lys Trp Arg Pro Asp
1               5

(2) INFORMATION FOR SEQ ID NO: 99:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 99:

Ala Ala Phe Tyr Lys Thr Phe Lys Thr Val
1               5                   10

(2) INFORMATION FOR SEQ ID NO: 100:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO
```

(v) FRAGMENT TYPE: N-terminal (xi) SEQUENCE DESCRIPTION: SEQ ID NO: 100:

Ala Ala Phe Tyr Lys Thr Phe Lys
1               5

(2) INFORMATION FOR SEQ ID NO:101:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 101:

Ala Phe Tyr Lys Thr Phe Lys Thr
1               5

(2) INFORMATION FOR SEQ ID NO:102:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 102:

Phe Tyr Lys Thr Phe Lys Thr Val
1               5

(2) INFORMATION FOR SEQ ID NO:103:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 103:

Lys Thr Val Glu Pro Thr Gly Lys Arg Phe Leu Leu
1               5                   10

(2) INFORMATION FOR SEQ ID NO:104:

(i) SEQUENCE CHARACTERISTICS:
        (A) LENGTH: 8 amino acids
        (B) TYPE: amino acid (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 104:

Lys Thr Val Glu Pro Thr Gly Lys
1               5

(2) INFORMATION FOR SEQ ID NO:105:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 105:

Thr Val Glu Pro Thr Gly Lys Arg
1               5

(2) INFORMATION FOR SEQ ID NO:106:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 106:

Val Glu Pro Thr Gly Lys Arg Phe
1               5

(2) INFORMATION FOR SEQ ID NO:107:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 107:

Glu Pro Thr Gly Lys Arg Phe Leu
1               5

(2) INFORMATION FOR SEQ ID NO:108:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 108:

Pro Thr Gly Lys Arg Phe Leu Leu
1               5

(2) INFORMATION FOR SEQ ID NO:109:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 109:

Leu Pro Met Ile Trp Ala Gln Lys Thr Asn Thr Pro
1               5                   10

(2) INFORMATION FOR SEQ ID NO:110:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 110:

Leu Pro Met Ile Trp Ala Gln Lys
1               5

(2) INFORMATION FOR SEQ ID NO:111:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 111:

Pro Met Ile Trp Ala Gln Lys Thr
1               5

(2) INFORMATION FOR SEQ ID NO:112:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 112:

Met Ile Trp Ala Gln Lys Thr Asn
1               5

(2) INFORMATION FOR SEQ ID NO:113:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 113:

Ile Trp Ala Gln Lys Thr Asn Thr
1               5

(2) INFORMATION FOR SEQ ID NO:114:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 114:

Trp Ala Gln Lys Thr Asn Thr Pro
1               5

(2) INFORMATION FOR SEQ ID NO:115:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 115:

```
Ala Leu Arg Glu Tyr Arg Lys Lys Met Asp Ile Pro Ala Lys Leu
 1               5                  10                  15
```

(2) INFORMATION FOR SEQ ID NO:116:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 116:

```
Ala Leu Arg Glu Tyr Arg Lys Lys
 1               5
```

(2) INFORMATION FOR SEQ ID NO:117:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 117:

```
Leu Arg Glu Tyr Arg Lys Lys Met
 1               5
```

(2) INFORMATION FOR SEQ ID NO:118:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 118:

Arg Glu Tyr Arg Lys Lys Met Asp
1               5

(2) INFORMATION FOR SEQ ID NO:119:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 119:

Glu Tyr Arg Lys Lys Met Asp Ile
1               5

(2) INFORMATION FOR SEQ ID NO:120:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 120:

Tyr Arg Lys Lys Met Asp Ile Pro
1               5

(2) INFORMATION FOR SEQ ID NO:121:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 121:

Arg Lys Lys Met Asp Ile Pro Ala
1               5

(2) INFORMATION FOR SEQ ID NO:122:

(i) SEQUENCE CHARACTERISTICS:
            (A) LENGTH: 8 amino acids
            (B) TYPE: amino acid

```
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 122:

Lys Lys Met Asp Ile Pro Ala Lys
1               5

(2) INFORMATION FOR SEQ ID NO:123:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 123:

Lys Met Asp Ile Pro Ala Lys Leu
1               5

(2) INFORMATION FOR SEQ ID NO:124:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 124:

Pro Gly Ile Arg Gly Pro Pro Pro
1               5

(2) INFORMATION FOR SEQ ID NO: 125:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal
```

-continued

```
    (xi) SEQUENCE DESCRIPTION: SEQ ID NO: 125:

Val Ala Phe Ser Asp Glu Met Val Pro Cys Pro Val Thr Thr Asp
1               5                  10                 15
Met Cys (2) INFORMATION FOR SEQ ID NO:126:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 126:

Val Glu Pro Thr Gly Lys Arg Phe Leu
1               5

(2) INFORMATION FOR SEQ ID NO: 127:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 127:

Gly Arg Gly Arg Gly Arg Gly Arg Gly Arg Gly Arg Gly Arg Gly
1               5                  10                 15
Arg Gly Arg Gly Arg
                20
```